US009001967B2

(12) United States Patent
Baturin et al.

(10) Patent No.: US 9,001,967 B2
(45) Date of Patent: Apr. 7, 2015

(54) SPECTRAL GRATING-BASED DIFFERENTIAL PHASE CONTRAST SYSTEM FOR MEDICAL RADIOGRAPHIC IMAGING

(71) Applicant: Carestream Health, Inc., Rochester, NY (US)

(72) Inventors: Pavlo Baturin, Rochester, NY (US); Mark E. Shafer, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 326 days.

(21) Appl. No.: 13/729,443

(22) Filed: Dec. 28, 2012

(65) Prior Publication Data
US 2014/0185746 A1    Jul. 3, 2014

(51) Int. Cl.
*A61B 6/03* (2006.01)
*G21K 1/06* (2006.01)
*G01N 23/04* (2006.01)
*A61B 6/00* (2006.01)
*A61B 6/06* (2006.01)

(52) U.S. Cl.
CPC . *A61B 6/484* (2013.01); *A61B 6/06* (2013.01); *A61B 6/4035* (2013.01); *A61B 6/4241* (2013.01); *A61B 6/482* (2013.01); *A61B 6/502* (2013.01); *G21K 1/06* (2013.01); *G21K 2207/005* (2013.01)

(58) Field of Classification Search
CPC ...... A61B 6/484; A61B 6/4291; A61B 6/032; A61B 6/482; A61B 6/4035; A61B 6/03; A61B 6/4241; G21K 1/06; G01N 23/04; G01N 23/20075; G01N 23/046; G01N 23/207

USPC ............ 378/36, 62, 5, 156, 19, 35, 37, 4, 87, 378/82, 71; 382/132

See application file for complete search history.

(56) References Cited

U.S. PATENT DOCUMENTS

| | | | | |
|---|---|---|---|---|
| 5,812,629 | A * | 9/1998 | Clauser | 378/62 |
| 7,453,981 | B2 * | 11/2008 | Baumann et al. | 378/62 |
| 7,639,786 | B2 * | 12/2009 | Baumann et al. | 378/145 |
| 7,817,777 | B2 * | 10/2010 | Baumann et al. | 378/62 |
| 8,515,002 | B2 * | 8/2013 | Huang et al. | 378/6 |
| 2007/0183560 | A1 * | 8/2007 | Popescu et al. | 378/5 |
| 2009/0092227 | A1 * | 4/2009 | David et al. | 378/36 |
| 2009/0116720 | A1 * | 5/2009 | Ritman | 382/132 |
| 2012/0020461 | A1 * | 1/2012 | Roessl et al. | 378/87 |
| 2013/0028378 | A1 * | 1/2013 | Stutman et al. | 378/62 |
| 2013/0259194 | A1 * | 10/2013 | Yip et al. | 378/37 |
| 2014/0185746 | A1 * | 7/2014 | Baturin et al. | 378/36 |
| 2014/0226782 | A1 * | 8/2014 | Stutman et al. | 378/4 |
| 2014/0226783 | A1 * | 8/2014 | Ning et al. | 378/5 |
| 2014/0270060 | A1 * | 9/2014 | Date et al. | 378/36 |
| 2014/0270061 | A1 * | 9/2014 | Yamaguchi | 378/36 |
| 2014/0341347 | A1 * | 11/2014 | Radicke | 378/62 |
| 2014/0355740 | A1 * | 12/2014 | Koehiler et al. | 378/62 |

* cited by examiner

*Primary Examiner* — David A Vanore

(57) ABSTRACT

Embodiments of methods and apparatus are disclosed for obtaining a phase-contrast digital radiographic imaging system and methods for same that can include an x-ray source for radiographic imaging; a beam shaping assembly including a collimator and a source grating, an x-ray grating interferometer including a phase grating, and an analyzer grating; and an x-ray detector, where a single arrangement of the beam shaping assembly, the x-ray grating interferometer and a position of the detector is configured to provide spectral information (e.g. at least two images obtained at different relative beam energies).

18 Claims, 36 Drawing Sheets

SPECTRAL GRATING-BASED DIFFERENTIAL PHASE CONTRAST SYSTEM FOR MEDICAL RADIOGRAPHIC IMAGING

FIELD OF THE INVENTION

The application generally relates to digital x-ray imaging methods/system, and more specifically, to methods and/or systems for acquiring multiple image information of an object (e.g., medical radiographic imaging) using a grating-based differential phase contrast imaging technique.

BACKGROUND OF THE INVENTION

Conventional medical x-ray imaging devices are based on the attenuation through photoelectric absorption of the x-rays penetrating the object to be imaged. However, for soft tissues including vessels, cartilages, lungs, and breast tissues with little absorption, this provides poor contrast compared with bone images. This problem of low contrast in soft tissues can be addressed with phase contrast imaging (PCI) techniques.

The principle of PCI is based on the wave nature of x-rays, where refraction and diffraction properties need to be considered. As an electromagnetic wave, the x-ray is usually characterized by its frequency, amplitude, and phase. When an electromagnetic wave penetrates a medium, its amplitude is attenuated and its phase is shifted. In x-ray technology, the refractive index n of a material can be expressed by a complex number $$n = 1 - \delta + i\beta \quad (1)$$

The imaginary part $\beta$ contributes to the attenuation of the amplitude and the real part $\delta$ is responsible for the phase shift. It has been shown that $\delta$ is about $10^3$ to $10^4$ times larger than $\beta$. But in conventional medical imaging, only the information of $\beta$ is recorded while the information of $\delta$ is completely lost. In recent years, several PCI techniques have been explored to make use of the phase shift to form the image, which is expected to provide more information about the object. Additionally, the diagnostic capabilities can be improved if spectral imaging techniques were implemented. So far, spectral imaging, which implies the x-ray acquisition at different mean energies of x-ray spectra (e.g., dual energy technique) have been primarily utilized in conventional absorption type of imaging.

SUMMARY OF THE INVENTION

An aspect of this application is to advance the art of medical radiographic imaging.

Another aspect of this application to address in whole or in part, at least the foregoing and other deficiencies in the related art.

It is another aspect of this application to provide in whole or in part, at least the advantages described herein.

Another aspect of the application is to provide methods and/or apparatus embodiments for digital radiographic medical imaging. Another aspect of the application is to provide phase contrast imaging methods and/or apparatus embodiments that can implement spectral imaging. Another aspect of the application is to provide methods and/or apparatus embodiments that can provide an energy-resolving detector at a single plane or position and collect images for two different mean energies with a single x-ray exposure. Another aspect of the application is to provide methods and/or apparatus embodiments for detuned multi-energy slot-scanning phase contrast imaging for large field of view (FOV) (e.g., greater than 100 mm square) radiographic medical imaging.

In accordance with one embodiment, the invention can provide a digital radiographic (DR) phase-contrast imaging (PCI) system that can include an x-ray source for radiographic imaging, a beam shaping assembly comprising a source grating G0, and an x-ray grating interferometer including a phase grating G1 and an analyzer grating G2, where a single arrangement of the beam shaping assembly, the x-ray grating interferometer and a position of the detector is configured to provide at least two images obtained at different relative beam energies.

In accordance with one embodiment, the invention can provide a method that can include providing an x-ray generator for radiographic imaging, providing a beam shaping assembly comprising a beam limiting apparatus and a source grating G0, providing an x-ray grating interferometer comprising a phase grating G1, and an analyzer grating G2, offsetting a pitch of the analyzer grating G2 relative to a pitch of an interference pattern produced by the phase grating G1 at a prescribed distance from the phase grating G1, and generating at least two images obtained at different relative beam energies by scanning the x-ray grating interferometer and an energy resolving detector once where an arrangement of the beam shaping assembly, the x-ray grating interferometer and a position of the detector is unchanged during the scan.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DESCRIPTION OF EXEMPLARY EMBODIMENTS

Figure 1:
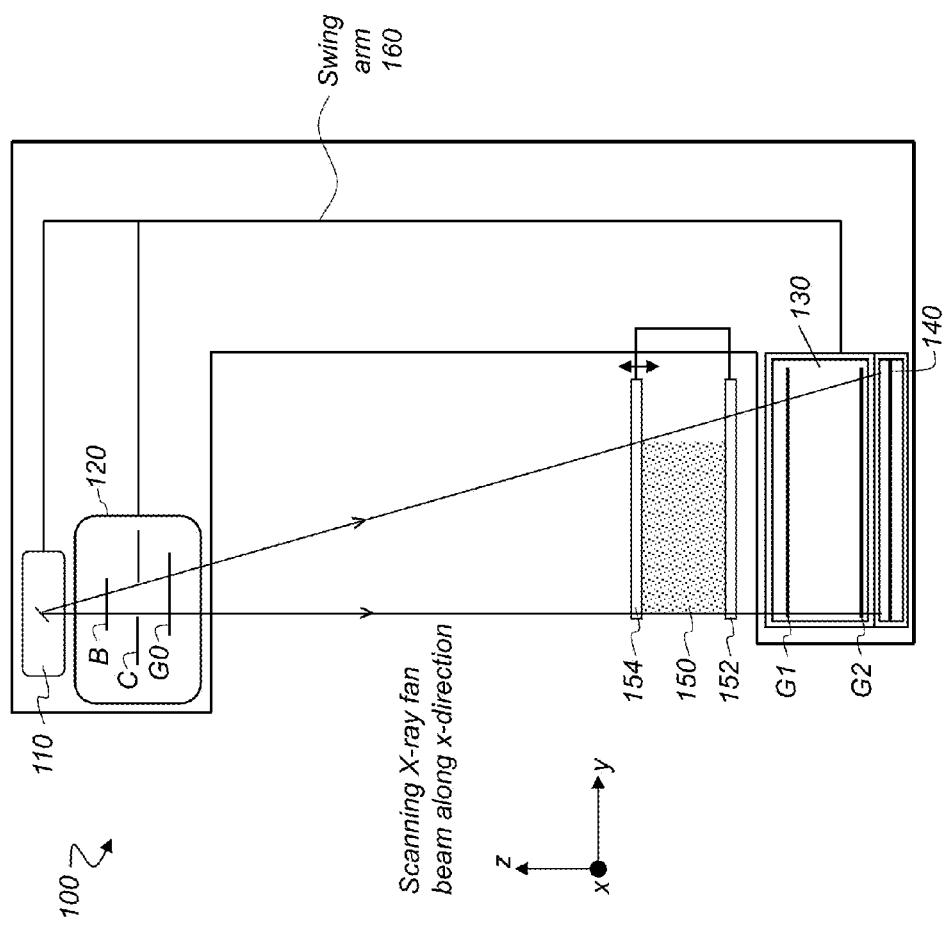
FIG. 1 is a diagram that shows a side view of an exemplary embodiment of a scanning-slot phase contrast digital mammography imaging system according to the application.

The following is a detailed description of exemplary embodiments according to the application, reference being made to the drawings in which the same reference numerals identify the same elements of structure in each of the several figures.

To be useful for clinical imaging, the phase contrast imaging systems must meet various requirements including: (i) use of a standard broadband x-ray source; (ii) a large field of view (FOV) of many centimeters (e.g., 24 cm×30 cm for a typical mammography system); (iii) a reasonably compact design comparable to current radiographic imaging systems (e.g., the source-to-detector distance is about 65 cm for a typical mammography system); and/or (iv) a reasonable exposure time and dose (e.g., the mean exposure for a typical mammography system is about 5 mR).

1. System Configuration

FIG. 1 is a diagram that shows an exemplary embodiment of a slot-scanning phase-contrast imaging system in accordance with the application. As shown in FIG. 1, a perspective view of a slot-scanning phase-contrast digital imaging system 100 can be used for mammography. The system 100 can include a conventional x-ray tube 110 for mammography imaging, a beam shaping assembly 120 comprising a filter or a tunable monochromator B, a collimator C, and a source grating G0, an x-ray grating interferometer 130 comprising a phase grating G1 and an analyzer grating G2, and an x-ray detector 140. The filter or a tunable monochromator B can be positioned after the collimator C. The three gratings (e.g., G0, G1, and G2) can be aligned in such a way that the plane and the grating bars of these gratings are parallel to each other. An object 150 (e.g., a breast) can be supported by a supporting plate 152 and is compressed by a compression paddle 154, which can be moved and adjusted (e.g., vertically).

Figure 2:
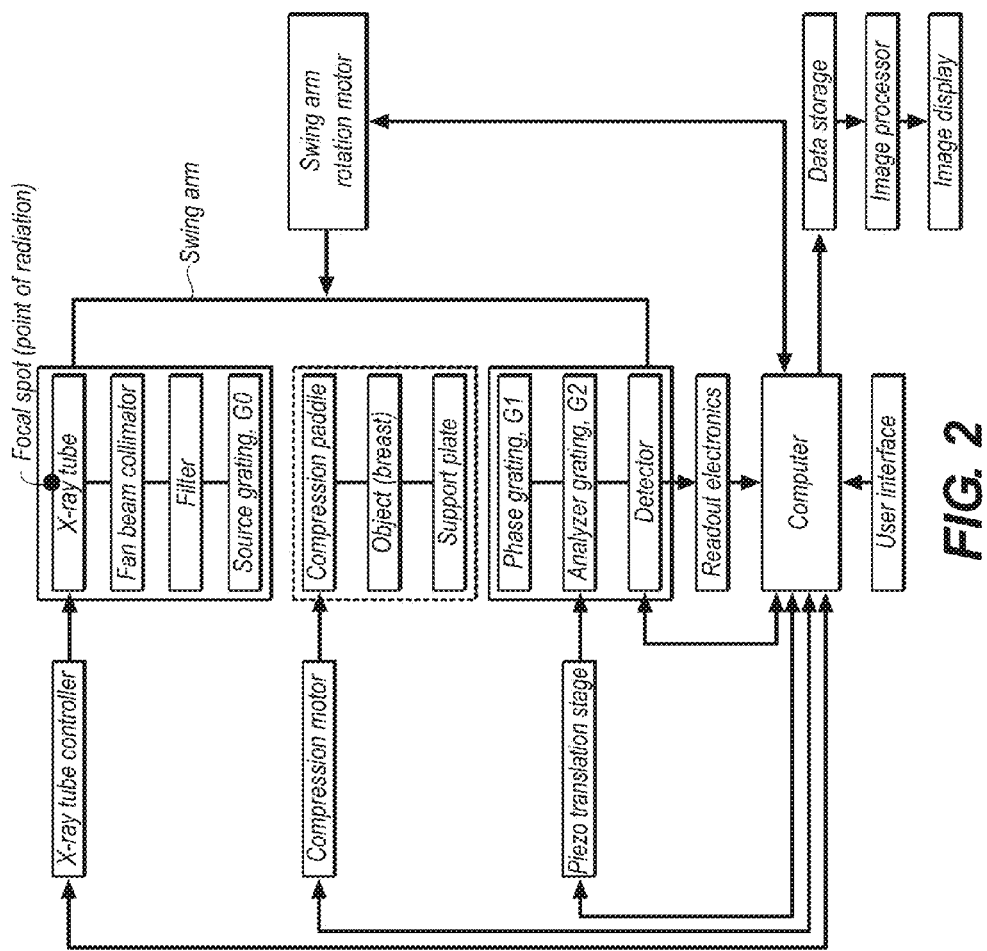
FIG. 2 is a diagram that shows a functional block diagram of an embodiment of a slot-scanning grating-based phase contrast digital mammography imaging system as shown in FIG. 1.

FIG. 2 is a functional block diagram that shows an exemplary embodiment of a slot-scanning phase-contrast imaging system. FIG. 2 shows a functional block diagram of the imaging system 100 used for mammography.

As shown in FIG. 1, the x-ray tube 110, the beam shaping assembly 120, the grating interferometer 130, and the detector 140 can move with a prescribed three-dimensional relationship to a radiation source. For example, the x-ray tube 110, the beam shaping assembly 120, the grating interferometer 130, and the detector 140 can be attached to a swing arm 160. The swing arm 160 can pivot around an axis co-axial with the focal spot of the x-ray tube 110. The x-ray tube 110 can be mounted at an angle with respect to the horizontal arm extension to illuminate an area of interest. The x-ray beam can be collimated to a narrow fan covering the interferometer 130 (e.g., gratings) and the active area of the detector 140 (e.g., about 24-cm long and 1-cm wide) by the collimator C. The entrance beam of the x-ray tube 110 can be slightly wider than the detector 140 and/interferometer 130 in order to reduce detector motion artifacts resulting from the edge of the detector 140 not being perfectly aligned with the collimator C at all times during the scan of an object.

2. System Components

Figure 3:
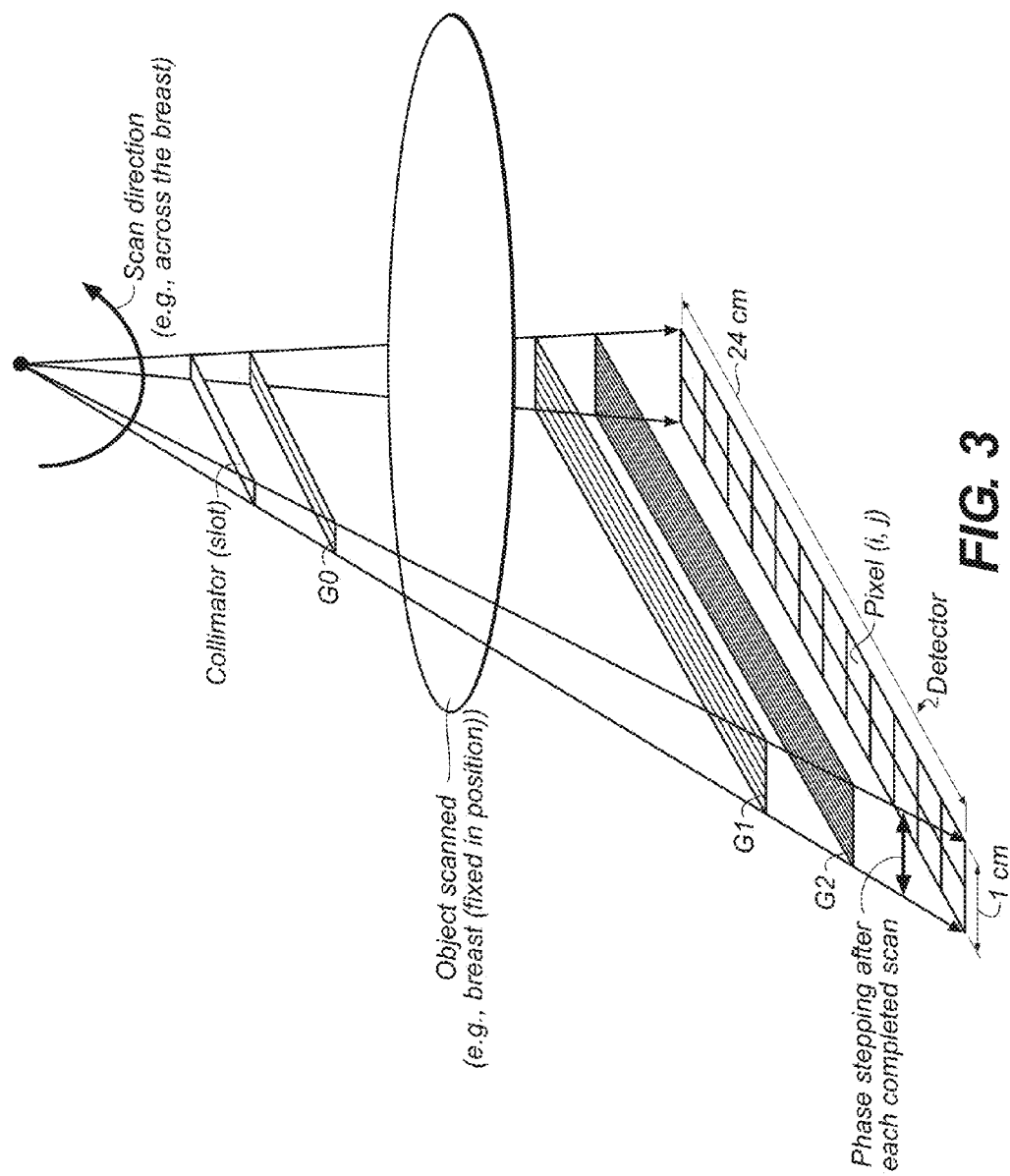
FIG. 3 is a diagram that shows an exemplary embodiment of a slot-scanning grating-based phase contrast digital mammography imaging system according to the application.
Figure 4:
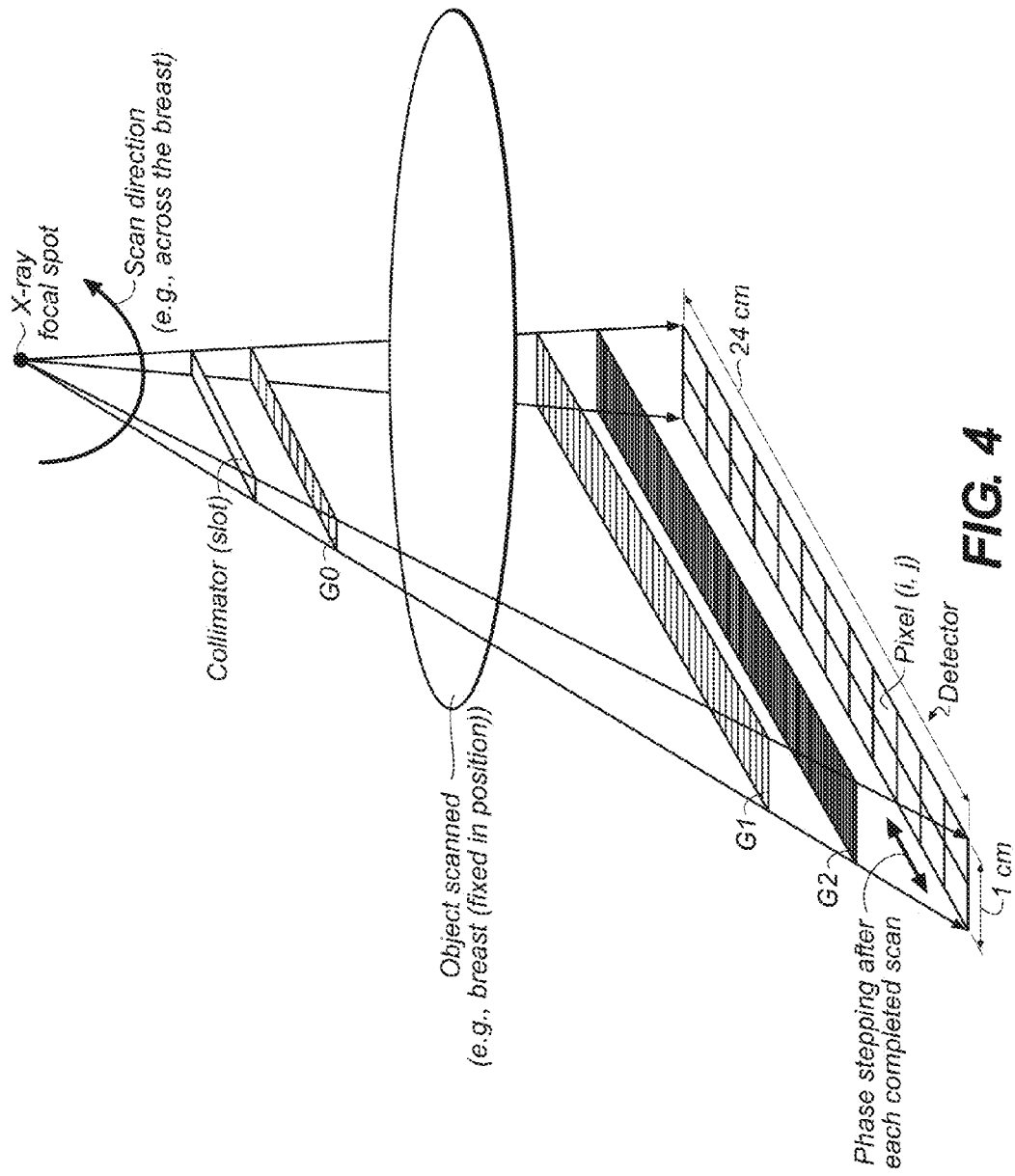
FIG. 4 is a diagram that shows another exemplary embodiment of a slot-scanning grating-based phase contrast digital mammography imaging system according to the application.

FIG. 3 is a diagram that shows a sectional illustration of an exemplary embodiment of components of a slot-scanning phase-contrast digital mammography imaging system in accordance with the application. FIG. 4 is a diagram that shows a sectional illustration of another exemplary embodiment of components of a slot-scanning phase-contrast digital mammography imaging system in accordance with the application. One difference between the imaging system of FIG. 3 and the imaging system shown in FIG. 4 is that the orientation of the grating bars of the gratings (e.g., the three gratings G0, G1, and G2) in FIG. 4 are parallel to the scan direction of the swing arm 160 (e.g., the x-ray fan beam), instead of being perpendicular to the scan direction of the swing arm 160 in FIG. 3.

(a) X-Ray Source

As shown in FIG. 1, the x-ray source 110 can be a conventional x-ray source. For example, the x-ray source 110 can be a polychromatic x-ray tube for mammography imaging. In this example, the x-ray source 110 can have a rotating anode made of tungsten (W), molybdenum (Mo), rhodium (Rh), or an alloy of heavy-element materials. The area of the focal spot can be between 0.01 mm$^2$ and 1.0 mm$^2$.

(b) Filter and Monochromator

Beside inherent filtration associated with the x-ray tube 110, additional filtration (e.g., by the filter B) can be optionally used to spectrally shape the x-ray beam into a narrow-bandwidth beam to reduce or eliminate the unnecessary soft x-rays that are mostly absorbed by the patient and contribute to the radiation dose received during the examination, and/or the hard x-rays that can reduce the quality of the image. Exemplary typical filter materials are aluminum (Al), molybdenum (Mo), rhodium (Rh), silver (Ag), and other metals.

Alternatively, the filter B can be a tunable monochromatic x-ray filter that can be used with a divergent polychromatic x-ray source to produce monochromatic x-rays with a narrow spectrum centered at a selectable energy with a bandwidth of 1-3 keV.

(c) Gratings

As shown in FIG. 1, the imaging system 100 can include three gratings. In one embodiment, the source grating G0 can have absorbing gold bars, the phase grating G1 can be made of silicon, and the analyzer grating G2 can be made of absorbing gold bars. However, other materials can be used as know to one skilled in the art. The source grating G0 can be placed close to the x-ray source 110. The second grating G1 and the third grating G2 can have a fixed distance in between, for example, by being mechanically coupled together, electromechanically connected or rigidly coupled together. Similarly, the source grating G0 and the interferometer 130 can be coupled to have a variable, but known distance therebetween.

The source grating G0 can allow the use of a large incoherent x-ray source as the x-ray source 110 because the source grating G0 can create an array of individual line sources that each can provide sufficient spatial coherence for the interferometric contrast. The images created by the source grating G0 generated line sources can be superimposed congruently in the detector plane at the detector 140 leading to a gain in intensity (e.g., controllable interference).

The phase grating G1 can operate as a beam splitter and divide the incoming beam essentially into the ±1 diffraction orders. These two ±1 diffracted beams can interfere and form a periodic interference pattern in the plane of the second grating G2 through the Talbot self-imaging effect. When an object is inserted in the x-ray beam path, the position of the fringe pattern would change. As the change of the fringe position in the micron range is not determined with a common detector, an analyzer second grating G2 can be placed at a specific Talbot distance from the phase first gating G1 to enable the transform of fringe positions into intensity modulations on the detector 140 located directly behind the second grating G2 with the phase stepping technique.

As the source grating G0 is disposed close to the x-ray source 110 and the collimator C, the size the source grating G0 can be small (e.g., about 1 cm×0.5 cm) because of the small angle subtended by the x-ray fan. For an exemplary (e.g., mammography) application, the FOV can be 24 cm×30 cm. Since the object is located close to the interferometer formed by gratings G1 and G2, the size of these gratings should match the FOV. Given the state of art for standard photolithography techniques, repeatable fabrications of such large-area gratings G1 and G2 (e.g., 24 cm×30 cm) with high or sufficient yield and an acceptable uniformity are not trivial. To address this fabrication problem, a standard 6 or 8 inch-silicon wafer can be used to fabricate multiple small gratings (e.g., each with an area of 8 cm×1 cm) within a square of 8 cm×8 cm. By abutting three pieces of small gratings together, a long and narrow grating (e.g., 24 cm×1 cm) can be repeatedly obtained with acceptable uniformity.

Figure 5:
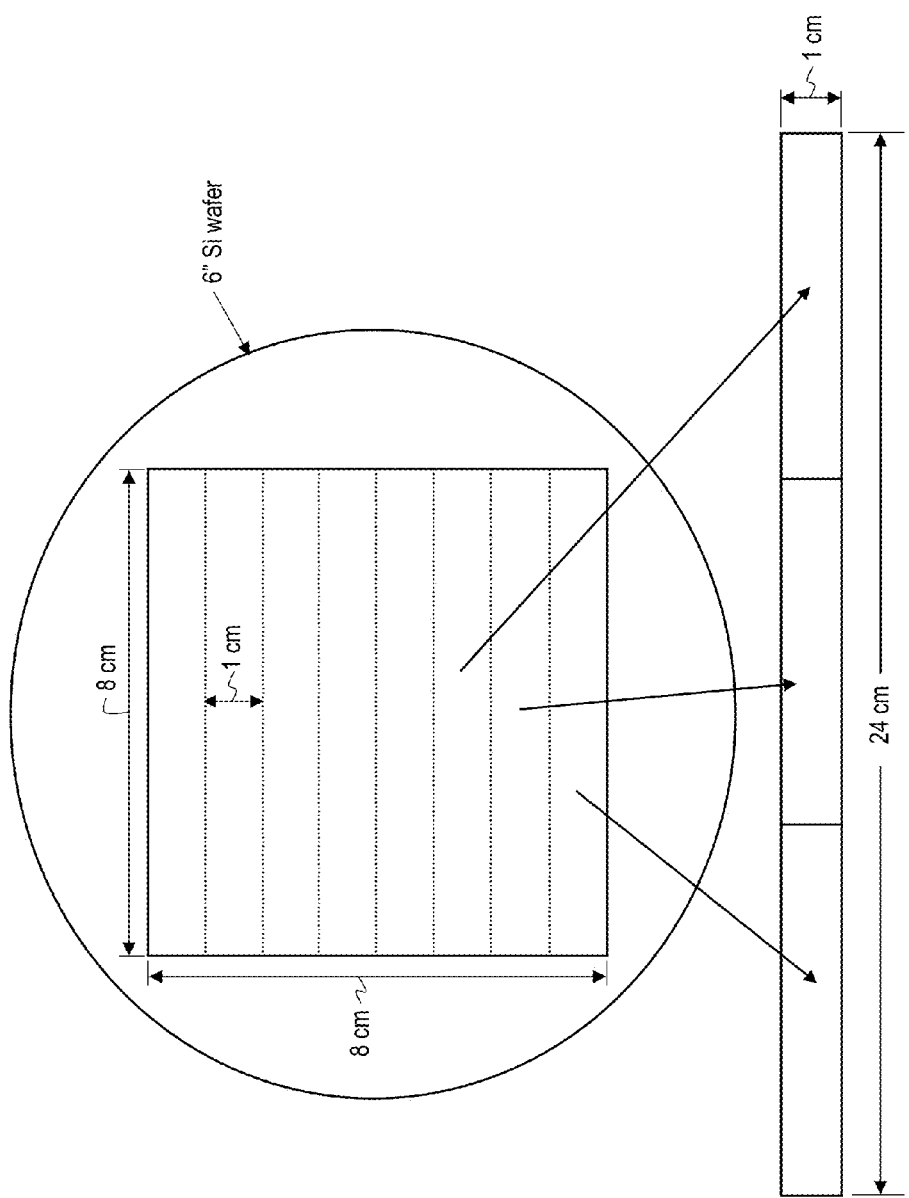
FIG. 5 is a diagram that shows an embodiment of a long and narrow grating (e.g., formed by abutting two or more small gratings together) according to the application.

FIG. 5 is a diagram that shows an embodiment of a long and narrow grating (e.g., formed by abutting two or more small gratings together) according to the application. As shown in FIG. 5, one embodiment of the G1 grating or G2 grating can be formed using a standard silicon wafer. In one embodiment, a standard 8" wafer can be used to provide the long and narrow gratings G1 and G2.

Figure 6A:
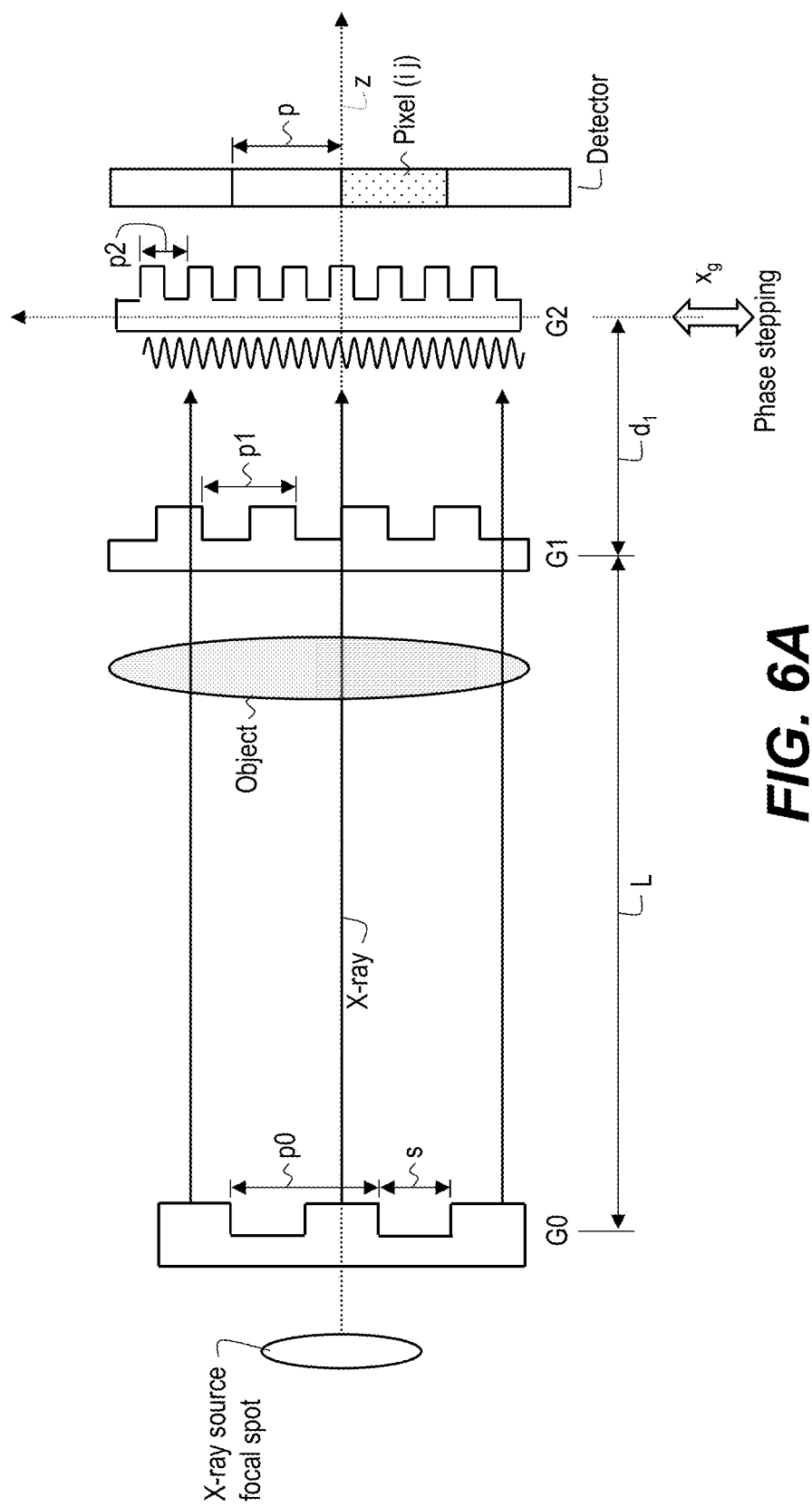
FIG. 6A is a diagram that shows a schematic of an exemplary three-grating phase contrast imaging system.

FIG. 6A is a diagram that shows a schematic of an exemplary three-grating phase contrast imaging system (e.g., interferometer). As shown in FIG. 6, three gratings, namely, the source grating G0 having absorbing gold bars, phase grating (or beam splitter) G1 made of silicon, and analyzer grating G2 having absorbing gold bars are used. The gratings are made from silicon wafers using standard photolithography techniques, and subsequently electroplating to fill the grooves with gold (G0 and G2). The interferometer is formed by G1 and G2. The plane and the grating bars of these three gratings are parallel to each other.

The source grating G0 allows the use of large incoherent x-ray sources since it creates an array of individual line sources each providing enough spatial coherence for the interferometric contrast. The images created by each line source are superimposed congruently in the detector plane leading to a gain in intensity. The phase grating G1 acts as a beam splitter and divides the incoming beam essentially into two first diffraction orders that interfere and form periodic fringe patterns in planes perpendicular to the optical axis (z).

Based on the Talbot effect, the periodic fringe pattern, which is called the self image of the phase grating G1, will have its highest contrast at the first Talbot distance $d_1$ behind G1. Assuming that the phase shift undergone by x-rays passing through the grating bars of G1 is π, the first Talbot distance is given by $$d_1 = \frac{p_1^2}{8\lambda} \quad (2)$$

where $p_1$ is the period of G1 and λ is the wavelength of x-ray for plane waves. The period of the fringe pattern ($p_2$) at the plane of the analyzer grating G2 placed at a distance of $d_1$ from G1 is approximately half the period of G1. The analyzer grating G2 has approximately the same period of the fringe pattern ($p_2$).

Figure 7:
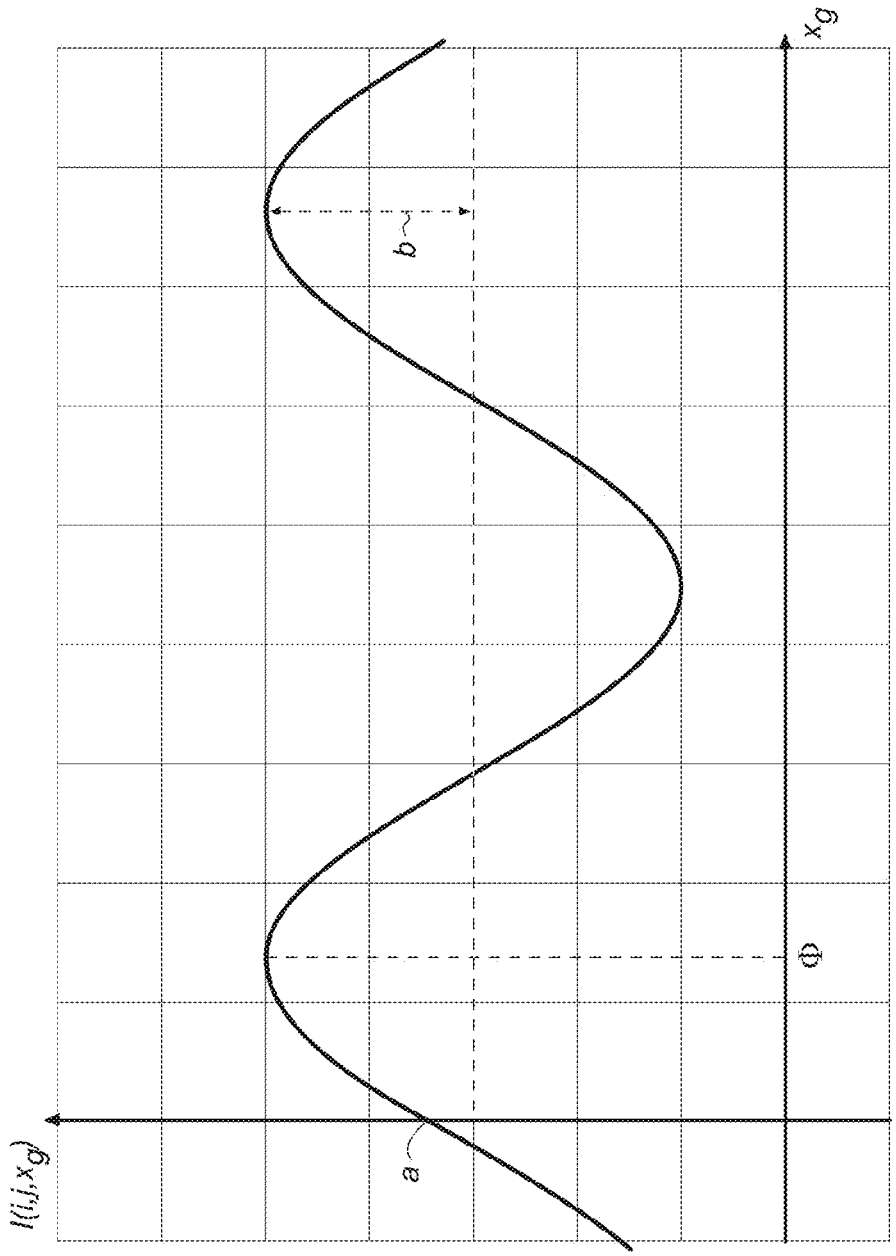
FIG. 7 is a diagram that shows intensity variation for one detector pixel (i, j) when one of the gratings (e.g., G2) is scanned along $x_g$ and the corresponding Fourier series coefficients.

When an object is placed in the beam path, the incoming x-ray wavefront can be locally distorted by the object. Where the wavefront is distorted, the fringes formed by the phase grating G1 are displaced from their unperturbed positions. The fringe displacements are transformed into intensity variations by the analyzer grating G2 placed at a distance $d_1$ from the phase grating G1. This allows the use of an x-ray detector placed just behind the analyzer grating G2 with much larger pixels than the spacing of the fringes. Using the phase stepping technique, scanning the lateral position $x_g$ of one of the gratings over one period of the grating (here the analyzer grating G2) causes the recorded signal in each pixel to oscillate as a function of $x_g$ as shown in FIG. 7. FIG. 7 is a diagram that shows intensity variation for one detector pixel (i, j) when one of the gratings (e.g., G2) is scanned along $x_g$ and the corresponding Fourier series coefficients a, b, and φ. The phase φ of the oscillation in each pixel is a measure of the wavefront phase gradient, while the average detector signal a in each pixel over the grating scan is equivalent to the conventional absorption image. The total phase shift of the object can thus be retrieved by a single one-dimensional integration along the direction x.

Figure 6B:
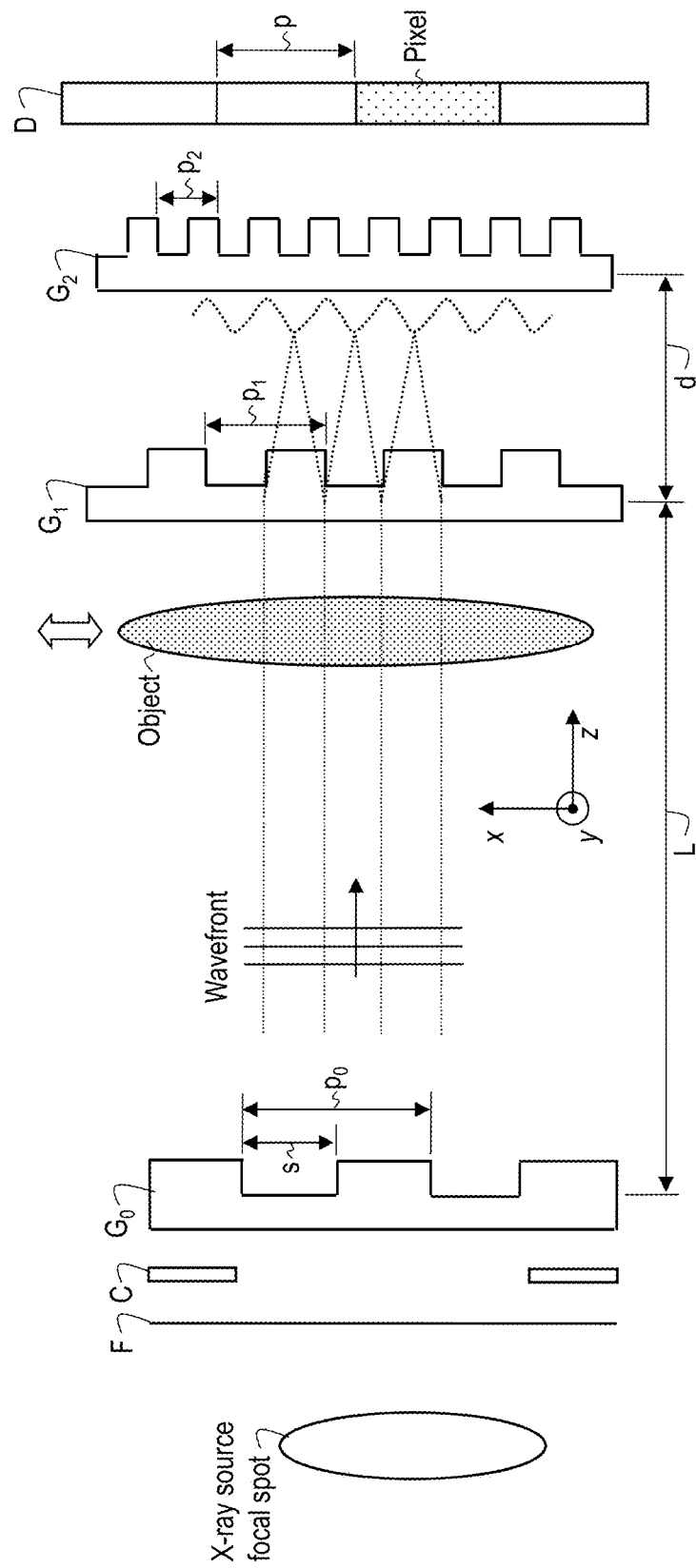
FIG. 6B is a diagram that shows a schematic of another exemplary three-grating phase contrast imaging system.

FIG. 6B is a diagram that shows a schematic of another exemplary three-grating phase contrast imaging system. As shown in FIG. 6B, a three-grating PCI system can include stationary G0, G1, and G2 gratings and an object to be imaged can be moved (e.g., across) relative to the stationary G0, G1, and G2 gratings. In FIG. 6B, F is optional additional filtration and C is an optional collimator or beam shaping apparatus.

(d) Detector

For the detector 140, either an indirect or a direct flat-panel x-ray detector can be used. An indirect flat panel detector can include a layer of scintillator made of CsI, $Gd_2O_2S$, or other scintillating phosphors coupled with an array of photodiodes (e.g., a-Si photodiodes) and switches (e.g., thin-film transistor (TFT) switches). The thickness of the scintillator layer can be between 80 um and 600 um. The pixel pitch of the detector is ranged from 20 to 200 um. On the other hand, a direct detector can include a photoconductor such as amorphous selenium (a-Se) or $PbI_2$ to produce electrical charges on the detection of an x-ray. The electromagnetic radiation detection process is considered direct because the image information is transferred from x-rays directly to electrical charges with no intermediate stage.

As an alternative to the flat-panel detectors, a charge-coupled device (CCD) based x-ray detector can be used as the detector 140. For example, the CCD based x-ray detector can include a scintillating screen.

For a slot-scanning system, a tiled CCD detector array operated in time delay integration (TDI) mode is preferred to enable continuous scanning motion and x-ray illumination during each scan. The detector array can be formed by tiling two or more CCD devices together and can be coupled to a scintillator layer and a fiber optic plate (FOP). The FOP is used to protect the CCD array from radiation damage.

A slot-scanning system with a beam width comparable to the pixel width would require an extremely high tube output. The TDI operating mode of the CCD can allow a significantly wider beam to be used. The detected x-rays are first transformed into light photons via the scintillator layer. The light photons are then transmitted to the CCD through the FOP producing electrons in the CCD in response to the light emission from the scintillator upon x-ray absorption. By moving the electronic charges from pixel-to-pixel across the CCD width (e.g., columns), in synchrony with (e.g., at the same velocity) but in the opposite direction of the scanning motion, the TDI mode can enable x-ray integration across the CCD width while maintaining the pixel resolution. When the charges reach the last row of the CCD, the accumulated charge is read out and digitized. For example, the detector array can include four CCDs, each having a size of 6 cm×1 cm, abutted along their narrow dimension to form a long and narrow detector (e.g., 24 cm×1 cm). Again, the typical pixel size is between 20 um and 200 um.

As another alternative to the flat-panel detectors, a linear photon counting gaseous detector using avalanche amplification process can be also used as the detector 140. Besides the use of gaseous detectors in photon counting technique, crystalline Si, CdTe, and CdZnTe can also be used in direct-conversion photon-counting detectors.

This exemplary single photon counting detection technique can discriminate noise in the detector 140 from a true x-ray photon interaction. By counting signals above a pre-defined threshold, an electronic noise free and efficient counting of single x-ray photons is achieved. When this detector type is used in a slot-scanning system according to embodiments of the application, significant reduction of patient dose and scattered radiation and/or a considerable increase in image quality in terms of contrast and spatial resolution can be obtained, as compared to the integrating detectors (such as direct and indirect flat-panel detectors and CCD devices).

3. Selection of System and Grating Parameters

Selections of grating parameters and the geometric system parameters in exemplary embodiments can be restricted by the choice of x-ray source, the limitation of the grating fabrication process, the practicality of the system size, the system performance requirements, and the conformation of physical laws. In summary, for a spherical x-ray wave, the system parameters and grating parameters should satisfy the following equations.

1. Spatial Coherence Requirement $$\ell_c = \frac{\lambda L}{s} \geq np_2, n = 1, 2, 3, \ldots \quad (3)$$

2. Period of Gratings $$p_0 = \frac{\lambda L}{np_2} + \sqrt{\left(\frac{\lambda L}{np_2}\right)^2 + \frac{2\lambda L}{n}}, n = 1, 2, 3, \ldots \quad (4)$$

$$p_1 = \frac{2p_0 p_2}{p_0 + p_2} \quad (5)$$

3. Phase Grating Requirement

The structure height of the silicon phase grating G1 has to be such that the x-rays passing through the grating bars undergo a prescribed phase shift or a phase shift of π (as an example), which results in the splitting of the beam into the ±1 diffraction orders.

$$h_1 = \frac{\lambda}{2\delta_{Si}} \quad (6)$$

Also, the structure height of gratings G0 and G2 should be large enough to provide sufficient absorption of x-ray (e.g., >75%) for selected or optimum system performance.

4. Talbot Self-Imaging Condition $$d_n = \frac{L\left[\frac{\left(n-\frac{1}{2}\right)p_1^2}{4\lambda}\right]}{L - \left[\frac{\left(n-\frac{1}{2}\right)p_1^2}{4\lambda}\right]}, n = 1, 2, 3, \ldots \quad (7)$$

The parameters shown in Eqs. (3)-(7) are as follows.
$l_c$=coherence length
λ=mean wavelength of x-ray radiation
L=distance between G0 and G1
s=slit width of G0
n=integer (Talbot order) $d_n$=Talbot distance between G1 and G2
$p_0$=period of G0
$p_1$=period of G1
$p_2$=period of G2
$h_0$=structure height of G0
$h_1$=structure height of G1
$h_2$=structure height of G2
$\delta_{Si}$=refractive index decrement of silicon By first selecting n, $p_2$, λ, and L based on system requirements and limitations on grating fabrication, other parameters, namely, s, $p_0$, $p_1$, $h_1$, $h_2$, $h_3$, and $d_n$ can then be determined. As an example, Table 1 lists exemplary system design parameters and grating parameters for an embodiment of a slot-scanning phase-contrast digital mammography system.

TABLE 1

| | |
|---|---|
| Mean E (keV) | 28 |
| Mean λ (nm) | 0.443 |
| L (mm) | 642 |
| $p_2$ (mm) | 2.0 |
| n | 1 |
| $d_n$ (mm) | 42.4 |
| s (um) | 7 |
| $p_0$ (um) | 30.3 |
| $p_1$ (um) | 3.75 |
| $h_0$ (um) | 42 |
| $h_1$ (um) | 36 |
| $h_2$ (um) | 26 |
| $l_c$ (um) | 4.0 |

4. Exemplary System Operations

Figure 8:
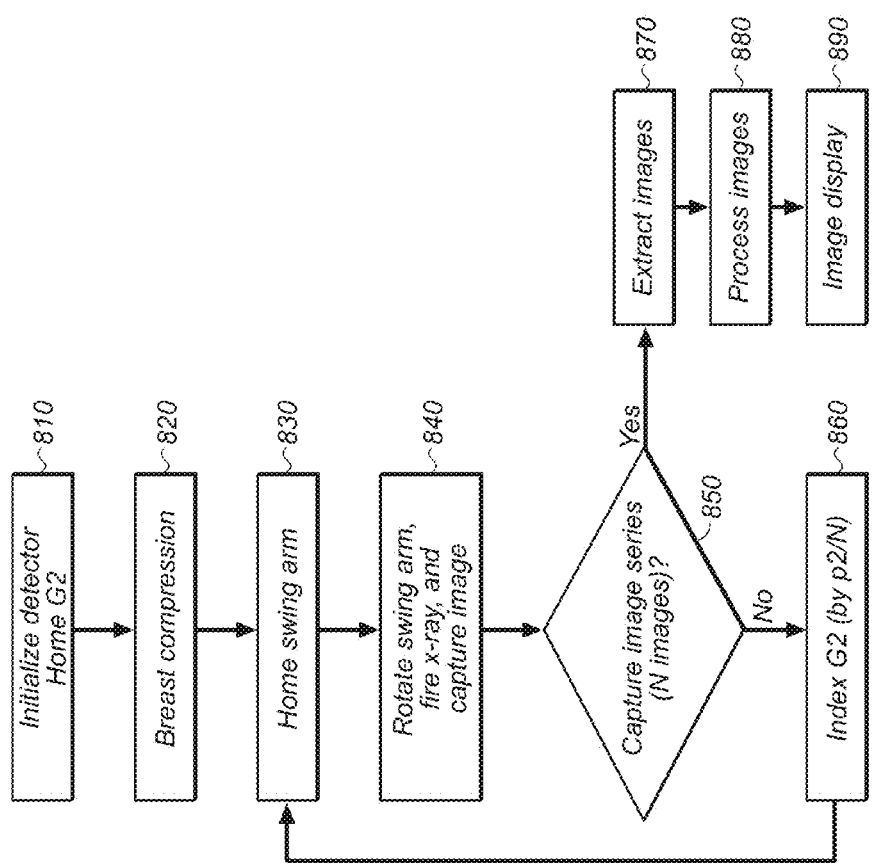
FIG. 8 is a flow chart that shows a method embodiment for operating a slot-scanning grating-based phase contrast digital mammography imaging system according to the application.

FIG. 8 is a flow chart that shows an embodiment of a method for operating a slot-scanning phase-contrast digital imaging system. The exemplary method embodiment of FIG. 8 will be described using and can be implemented by the system embodiment shown in FIG. 1 and FIG. 3, however the method is not intended to be so limited.

As shown in FIG. 8, after a process starts, the detector is initialized in preparation for exposure and the analyzer grating G2 is moved to a prescribed position or home position (operation block 810). Then, for mammographic medical images, the breast can be compressed (e.g., to improve image quality) (operation block 820). The swing arm 160 is set to an initial or home position (operation block 830). Thus, block 830 can position the x-ray tube 110, the beam shaping assembly 120, the x-ray grating interferometer 130 and the x-ray detector 140 that can be rigidly mounted to the swing arm 160. The x-ray beam can be scanned across the object as the swing arm 160 rotates in an arc like a pendulum covering the width of the object (e.g., about 30 cm) as shown in FIG. 3. When the x-ray beam completes a full scan across the object, the image data recorded by the detector 140 can be read out and stored in a memory unit of a computer (e.g., at the slot-scanning phase-contrast digital imaging system or at a wirelessly coupled control console having a processor, display and memory. In one embodiment, the detector is a long and narrow CCD based detector and can operate in the time delay integration (TDI) mode for signal detection. Then, it is determined whether the image series is complete (e.g., N images have been captured) in operation block 850. When the determination in block 850 is negative, using the phase stepping technique, as an example, the analyzer grating G2 (e.g., mounted on a piezo translation stage) is then moved laterally by a predetermined distance (step) before the next scan of the x-ray beam starts (operation block 860) and the process jumps back to block 830 where the swing arm 160 is returned to the initial pre-scan position or home position (or reversed in rotational direction) to be ready for the next scan in the image series.

When the determination in block 850 is affirmative because a predetermined number of cycles N (e.g., typically 5 to 8) of scanning and stepping are completed, the image data set can be extracted, processed, and displayed on a monitor (operation blocks 870, 880, 890). For example, the same image data set can be processed by an image processing unit of the computer to construct multiple images of the object including absorption contrast, differential phase contrast, phase shift contrast, and dark-field images, as described herein.

These absorption contrast, differential phase contrast, phase shift contrast, and dark-field images are complementary to each other can provide the necessary specificity to visualize subtle details in the object.

There are alternate ways to implement the phase stepping described in the method embodiment of FIG. 8. Exemplary alternate phase stepping implementations include but are not limited to: (i) moving grating G1 (instead of G2) in the direction perpendicular to both the optical axis and the grating bars of G1; (ii) rotating G1 and G2 together around an axis along the orientation of grating bars by an angle (e.g., the two gratings are kept in an aligned position with respect to each other or are fixed together mechanically); or (iii) moving the x-ray source in the direction perpendicular to both the optical axis and the grating bars of the gratings. These exemplary alternate phase stepping implementations can be implemented on the exemplary swing arm 160 configuration shown in FIG. 3.

Figure 9:
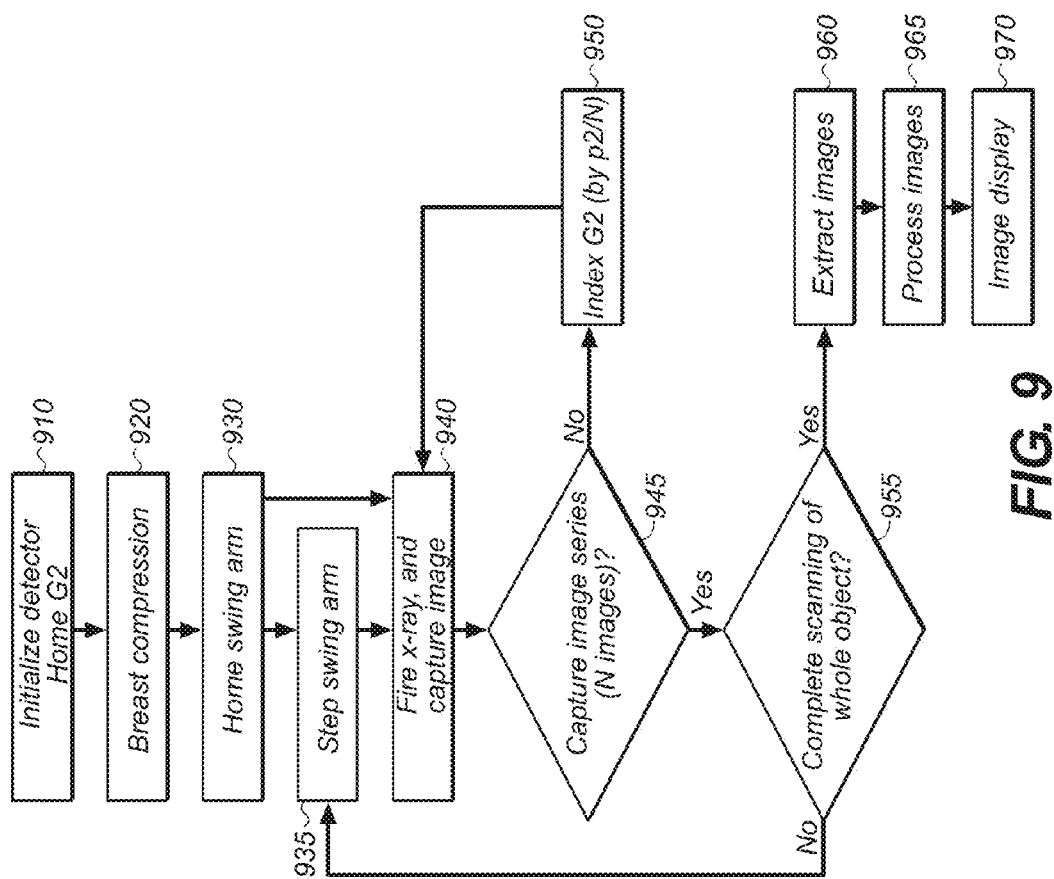
FIG. 9 is a flow chart that shows another method embodiment for operating a slot-scanning grating-based phase contrast digital mammography imaging system according to the application.

FIG. 9 is a flow chart that shows an embodiment of a method for operating a slot-scanning phase-contrast digital imaging system. The exemplary method embodiment of FIG.

9 will be described using and can be implemented by the system embodiment shown in FIG. 1 and FIGS. 3-4, however the method is not intended to be so limited.

FIG. 9 shows another "step-dither-step" mode of system operations where the swing arm can scan across the object in a step-wise motion. The distance of each step can be about the width of the detector. At each position of the swing arm, a series of x-ray exposure/image capture operations can be performed (e.g., N images captured) using the aforementioned phase stepping technique (e.g., move the analyzer grating G2 by p$_2$/N). Then, the swing arm moves to the next step position and another series of x-ray exposure/image capture operations is performed until the swing arm steps through and completes the whole object scan. Then, the raw image data set is extracted, processed, and displayed on a monitor. Alternatively, as the swing arm steps through the whole object, the raw images data subset can be extracted at the end of each "step", and the captured raw images can be processed and displayed on a monitor concurrently or at the completion of the last step.

As shown in FIG. 9, after a process starts, the detector is initialized in preparation for exposure and the analyzer grating G2 is moved to a prescribed position or home position (operation block 910). Then, an object can be positioned or for mammographic medical images, the breast can be compressed (e.g., to improve image quality) (operation block 920). The swing arm 160 is set to an initial or home position (operation block 930).

Then, the swing arm 160 is stepped to a current step position (operation block 933), the x-ray beam is fired to expose and capture an image of a portion of the object (operation block 940). Then, it is determined whether the image series is complete for that step (e.g., N images have been captured) in operation block 945. When the determination in block 945 is negative, using the phase stepping technique, as an example, the analyzer grating G2 (e.g., mounted on a piezo translation stage) is then moved laterally by a predetermined distance (e.g., p$_2$/N such as 2 mm/8=250 nm) and the process jumps back to block 940 where the x-ray beam is fired to expose and capture an image of a portion of the object.

When the determination in block 945 is affirmative because a predetermined number of cycles N (e.g., typically 5 to 8) of stepping and scanning are completed, the image data set can be stored and it can be determined in operation block 955 whether scanning is complete for the whole object. When the determination in block 955 is negative, the swing arm 160 is stepped to the next position (operation block 933) and operation blocks 940, 945 and 950 can be repeated. When the determination in block 955 is affirmative because the whole object has been scanned, the image data set can be extracted, processed, and displayed on a monitor (operation blocks 960, 965, 970). For example, the same image data set can be processed by an image processing unit of the computer to construct multiple images of the object including absorption contrast, differential phase contrast, phase shift contrast, and dark-field images, as described herein.

5. Image Formation and Image Retrieval

Without the object in place, the x-ray beam passes through the phase grating G1 and form interference fringes. Having the object in the beam path, the incoming x-ray wavefront is locally distorted by the object causing an angular deviation of the x-ray beam:

$$\alpha(x, y) = \frac{\lambda}{2\pi} \frac{\partial \Phi(x, y)}{\partial x} \quad (8)$$

Where the wavefront is distorted, these fringes are displaced from their unperturbed position by $$D(x,y)=d_n \cdot \alpha(x,y) \quad (9)$$

The fringe displacements are transformed into intensity values by an analyzer grating G2 placed at a distance d$_n$ from the phase grating G1. A two-dimensional detector with much larger pixels than the spacing of the fringes can be used to record the signal. Scanning the lateral position x$_g$ of one of the gratings (e.g., the analyzer grating G2) causes the recorded signal in each pixel to oscillate as a function of x$_g$. For each pixel (i, j), the signal oscillation curve can be expressed by a Fourier series, $$I_s(i, j, x_g) \approx a_s(i, j) + b_s(i, j)\cos\left(\frac{2\pi}{p_2}x_g + \phi_s(i, j)\right) \quad (10)$$

(with the object)

$$I_b(i, j, x_g) \approx a_b(i, j) + b_b(i, j)\cos\left(\frac{2\pi}{p_2}x_g + \phi_b(i, j)\right) \quad (11)$$

(without the object)

From Eqs. (10) and (11), the following images of the object can be retrieved. The transmission image is given by $$T(i, j) = \frac{a_s(i, j)}{a_b(i, j)} \quad (12)$$

The differential phase contrast image is given by $$\left(\frac{\partial \Phi}{\partial x}\right)_{i,j} = \frac{p_2}{\lambda d_n}(\phi_s(i, j) - \phi_b(i, j)) \quad (13)$$

Also, the phase shift image of the object can be obtained by simple one-dimensional integration along the pixel direction perpendicular to the grating bars, e.g., $$\Phi_{i,j} = \frac{p_2}{\lambda d_n} \int (\phi_s(i, j) - \phi_b(i, j))dx \quad (14)$$

Furthermore, a dark-field image is formed from higher-angle diffraction intensities scattered by the object. The information about the scattering power of the object is contained in the first Fourier amplitude coefficient, bs(i, j) of Is(i, j, x$_g$). Thus, the dark-field image can be obtained by $$V(i, j) = \frac{b_s(i, j)/a_s(i, j)}{b_b(i, j)/a_b(i, j)} \quad (15)$$

These four different images of the object can be derived from the same data set and can be complementary to each other to provide multiple information of the object enabling the visualization of subtle details in the object.

As described herein, embodiments of phase-contrast digital imaging systems and/or methods of using the same can provide various advantages according to the application. Embodiments of slot-scanning grating-based differential phase contrast systems and/or methods can significantly enhance the contrast of low absorbing tissues (e.g., the contrast between healthy and diseased tissues), which can be especially useful for mammography and orthopedic joints. Embodiments of slot-scanning grating-based differential phase contrast systems and/or methods can allow the use of small gratings and detectors to produce a large-area image. Embodiments can provide reduction in motion blur, scattered radiation, and patient dose without using a grid.

Embodiments of slot-scanning grating-based differential phase contrast systems and/or methods can use curved gratings and detectors circularly around the source focus to enable the design of a more compact system and reduce or eliminate the shadowing effect of the phase grating and/or the scan effect of the analyzer grating occurred in the edge regions of the image.

Certain exemplary embodiments for slot-scanning phase-contrast digital imaging systems and/or methods for using the same, e.g., see FIGS. 8 and 9, can employ step-dither-step approaches, where one of the gratings, either phase grating G1 or analyzer grating G2, can be stepped with respect to another. For example, when moving analyzer grating G2 where N is a number of steps (e.g., using a piezo translational stage) required to cover a period of grating G2, and the lateral size of the grating G2 is $l_{G2}$; then the scan of an object with lateral size S can use or require $S/l_{G2} \cdot N$ of x-ray exposures. For an exemplary S=20 cm breast and 8 phase steps for a 1 cm wide G2 grating at each position (or slice) of the swing arm, then 20/1.8=160 x-ray exposures are used to scan the whole object. Note that $S/l_{G2} \cdot N$ can be considered a sufficient or minimal number needed for a full scan. To properly stitch the slices into an image of the whole object, slight overlaps between slices can be required.

Both exemplary scanning embodiments described in FIGS. 8 and 9 have either the swing arm or the analyzer grating G2 return back to its initial (e.g., home) position after one slice of the object is scanned. Although, precision positioning of these devices (e.g., translational piezo drivers) can reach the nm scale, the multiple forward-backward types of motions can add up to significant spatial errors after the whole object scan is complete. To reduce or avoid spatial errors, continuous motion of the swing arm with minimal or no stepping of the analyzer grating is preferable. It is also preferable when the relative position of the gratings G1 and G2 does not change (e.g., no stepping) and/or the swing arm continuously moves across the object, which can reduce a scanning time.

Figure 11:
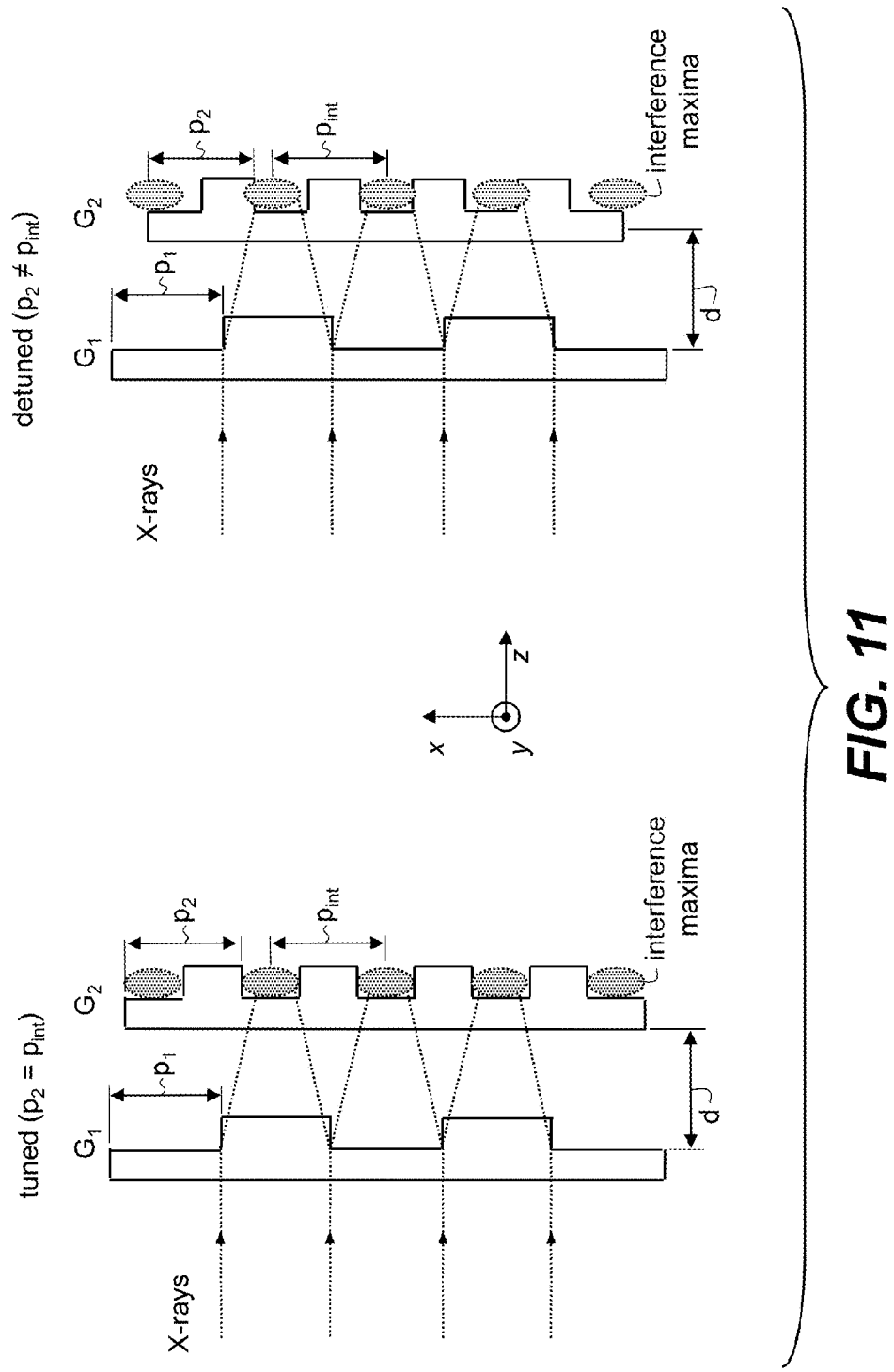
FIG. 11 is a diagram that illustrates schematics for exemplary embodiments of tuned phase-contrast digital imaging systems and exemplary embodiments of detuned phase-contrast digital imaging systems.

To implement continuous motion of the swing arm with fixed G1 and G2 gratings, exemplary embodiments of phase contrast imaging systems have to be detuned. In one exemplary embodiment, a detuned phase contrast imaging system can be understood to be an imaging system in which the pitch $p_2$ of the analyzer grating G2 is purposely controlled or fabricated to be unequal to a period of interference pattern $p_{int}$ at a Talbot distance behind the phase grating G1. In another exemplary embodiment, a detuned phase contrast imaging system can be understood to be an imaging system in which the pitch $p_2$ of the analyzer grating G2 is controlled or fabricated to be equal to a period of interference pattern $p_{int}$ at a Talbot distance behind the phase grating G1, but the analyzer grating G2 is positioned away from the corresponding Talbot distance. In certain exemplary embodiment, a detuned phase contrast imaging system can generate a periodic fringe pattern, where the fringe pattern occurs over a width or a portion of the width of the analyzer gating G2. Although a number of exposures for detuned grating based PCI system embodiments in a complete or partial scan of an object is about the same, positional errors and/or scanning time can be reduced relative to a tuned grating based PCI systems. FIG. 11 is a diagram that illustrates concepts of exemplary tuned and detuned phase contrast imaging systems. The analyzer grating G2 and the interference pattern can be approximated as a cosine waves with the frequencies $f_2=1/p_2$ and $f_{int}=1/p_{int}$, respectively. Then, the signal measured by detector, placed behind the analyzer grating, is:

$$I_s = \text{MTF}(f) \cdot [\cos(2\pi f_{int} x) \cdot \cos(2\pi f_2 x)] = \text{MTF}(f) \cdot [\cos(2\pi (f_{int}+f_2)x) + \cos(2\pi (f_{int}-f_2)x)]/2. \quad (16)$$

For example, MTF is a detector's modulation transfer function that can be approximated by: $\text{MTF}(f)=0.5 \cdot \text{erfc}[\alpha \ln(f/f_0)]$, where $\alpha$ is a slope of the MTF curve and $f_0$ is the spatial frequency at which MTF drops by 50%. The spatial frequency at $p_2$=2 um pitch of the analyzer grating is 500 cyc/mm. When summed with comparable frequency of interference pattern, it doubles, e.g., $f_{int}+f_2$=1000 cyc/mm. Exemplary values of $f_0$ in indirect charge integrating detectors can be typically between 1 and 2 cyc/mm, while value of $f_0$ can reach 5 cyc/mm in the case of direct photon counting detectors. That said, the detector will measure no signal at 1000 cyc/mm. Therefore, the only detectable signal is:

$$\text{MTF}(f) \cdot \cos(2\pi(f_{int}-f_2)x/2 \quad (17)$$

Figure 12:
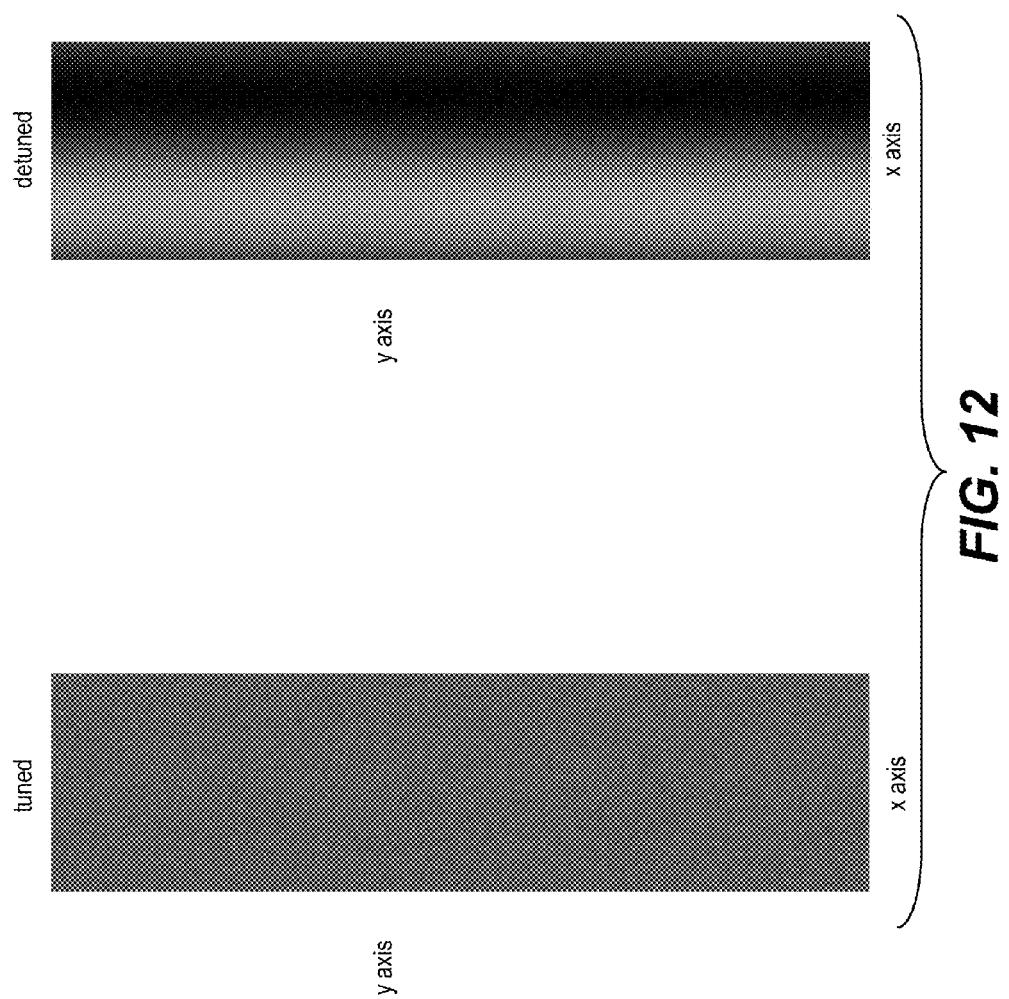
FIG. 12 is a diagram that illustrates examples of the open field images measured in the detector plane for tuned and detuned configurations of phase contrast imaging system embodiments.

In the case of a tuned phase contrast imaging system ($f_{int}=f_2$), the signal is increased or maximum. When measuring the open field in such configuration, the detector yields the uniform image. In the case of detuned phase contrast imaging system, the detected image will have a cosine pattern with a lower contrast caused by detector's MTF. The loss of the contrast depends on how strongly the system is detuned, i.e. $\Delta f = f_{int}-f_2$. FIG. 12 is a diagram that illustrates examples of the open field images measured in the detector plane for tuned and detuned configurations of a phase contrast imaging system embodiment. As shown in FIG. 12, an open field image for a tuned phase contrast imaging system embodiment can produce an unchanging or flat open field image across the analyzer grating G2. As shown in FIG. 12, the lateral size of an image is chosen to be equal to one period of fringe pattern as an example. In one embodiment, the phase contrast imaging system, $\Delta f$ can be <5%, <1% or <0.1%.

Figure 13B:
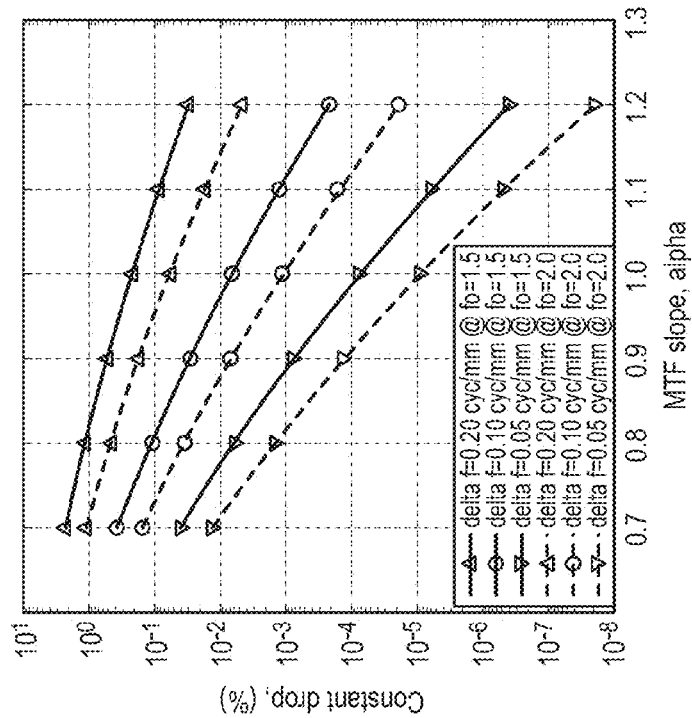
FIG. 13B is a diagram that shows the percentage of the contrast drop as a function of MTF slope α, spatial frequency f0 at 50% MTF drop, and the degree of the system detuning Δf.
Figure 13A:
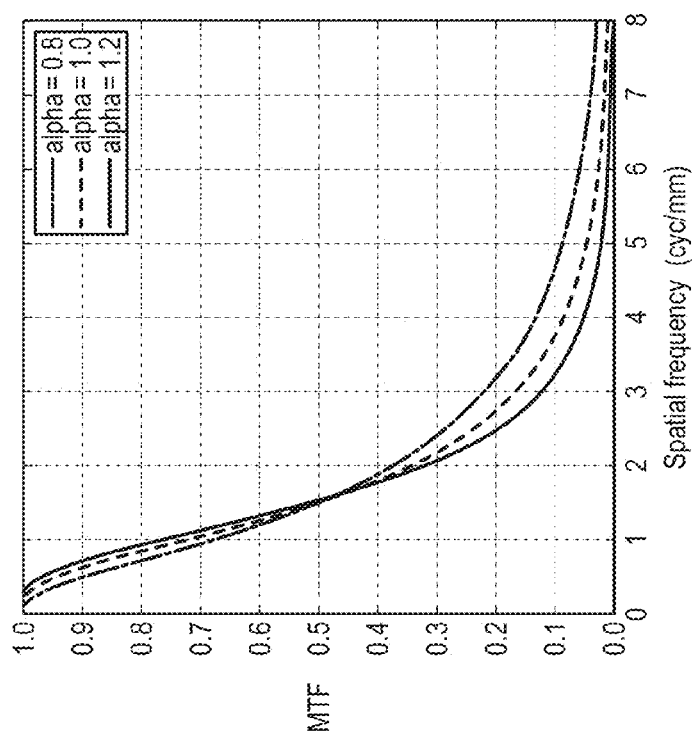
FIG. 13A is a diagram that shows several MTFs plotted for different alpha slopes.

The response of the detector as a function of the spatial frequency is important. FIG. 13A shows several MTFs plotted for different alpha slope (e.g., see equation 16). The MTF with a higher value of slope can have a longer plateau (e.g., slower reduction) for a spatial frequency below the half value frequency. The higher slope is typical for a detector with a better frequency response, for example direct conversion photon-counting detector in comparison to indirect detector. For a case of indirect detectors, the slope $\alpha$ is typically close to 1 and higher, while the half value frequency is in the range between 1.5 and 2 cyc/mm. FIG. 13B shows the percentage of the contrast drop as a function of MTF slope $\alpha$ and spatial frequency $f_0$. As expected, the drop in contrast relative to the maximum possible (e.g., at $\Delta f$=0) is less for smaller $\Delta f$. Also, the curves shown in FIG. 13 get even lower for higher $f_0$ (e.g., for a detector with higher quantum efficiency). Higher MTF slope $\alpha$ can further reduce the drop in contrast. The MTF slope $\alpha$ is typically close to 1 and higher. When the PCI system is implemented according to FIG. 3, the width of G2 grating can be selected based on $\Delta f$. If the width of G2 is set to be equal to one period of the measured fringe pattern, then for Δf=0.20, 0.10, or 0.05 cyc/mm the width of G2 can be 0.5, 1, or 2 cm, respectively. As described herein, to avoid the non-uniformity in grating fabrication, it is preferable to keep the width of the analyzer grating small. Therefore, the width of 1 cm with corresponding Δf=0.1 cyc/mm can be the most suitable, although, embodiments of the application are not intended to be so limited. Further, other sizes can be used when the width of G2 is equal to not one but two or more periods of interferometeric contrast.

In contrast to embodiments of tuned phase contrast imaging systems, embodiments of detuned system can only be implemented according to schematics shown in FIG. 3. The fringe patters in the detector plane has to be oriented such that the arms swings laterally across the pattern. While PCI implementation depicted on FIG. 4 is suitable for tuned phase contrast imaging system, it cannot be applied to detuned PCI system. Additionally, in case of embodiments of detuned PCI systems, the analyzer grating G2 and the detector D can be moved together (e.g., using an attached translational piezo driver) to simultaneously move them in the direction of the x-ray beam (e.g., z axis) such that the frequency (Δf) of fringe pattern in the detector plane can be adjusted.

When the width of the analyzer grating G2 is chosen, for example 1 cm, it might be challenging to precisely fabricate the grating with the pitch that would form expected frequency of the fringe pattern at the detector plane, for example 0.1 cyc/mm. In one embodiment, when the pitch G2 is slightly off of the desired or selected dimensions, the phase contrast imaging system can be tweaked by shifting the analyzer grating G2 along the beam axis (e.g., axis z) relative to the phase grating G1. By shifting the analyzer grating G2 along the beam axis, the analyzer grating G2 can peak at different z position of the interference pattern formed by phase grating G1. In other words, in certain exemplary embodiments, the different frequency of interference pattern, $f_{int}$, is used to form the desired fringe pattern at the detector plane.

Figure 14:
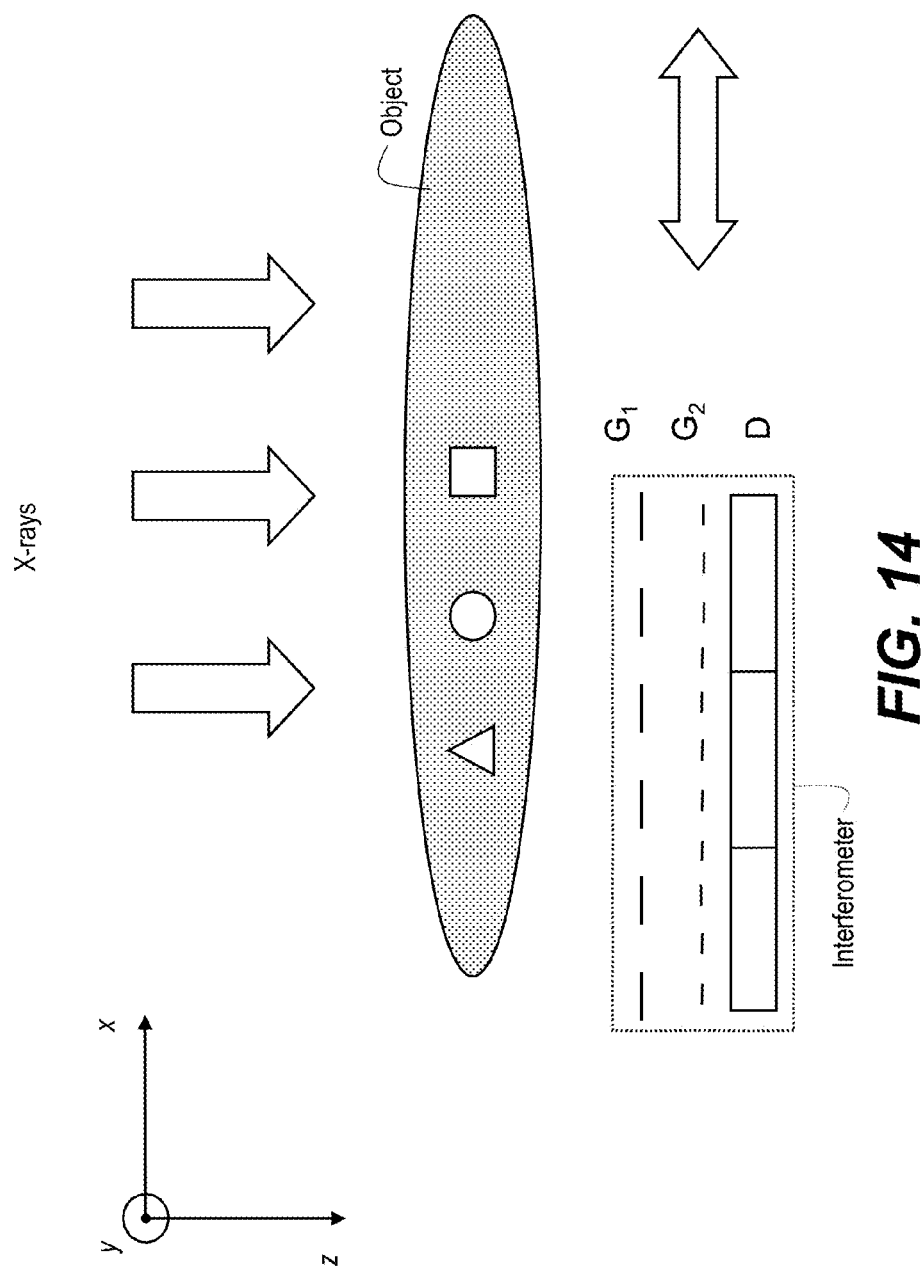
FIG. 14 is a diagram that illustrates exemplary motion of interferometer with respect to objects or vise versa for a phase contrast imaging system embodiment.
Figure 15:
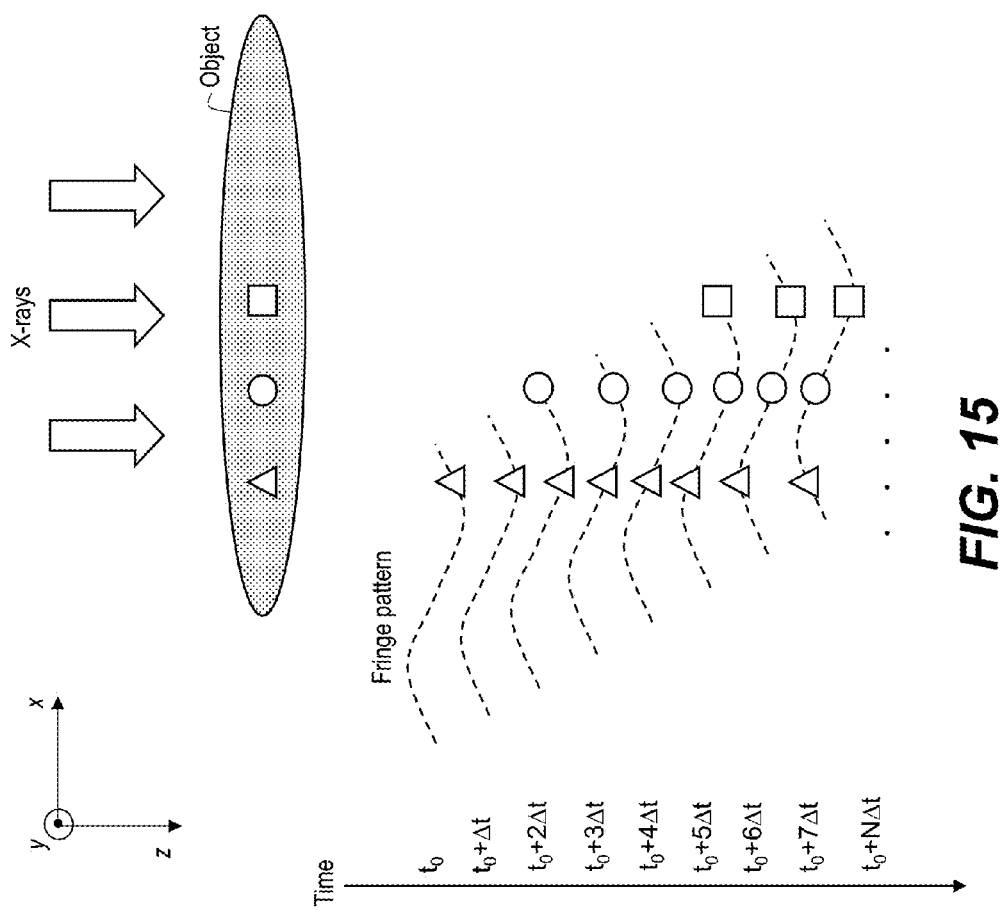
FIG. 15 is a diagram that illustrates exemplary of object scan schematics that project individual slices of the object onto one-period fringe pattern measured in the detector plane according to embodiments of the application.
Figure 16:
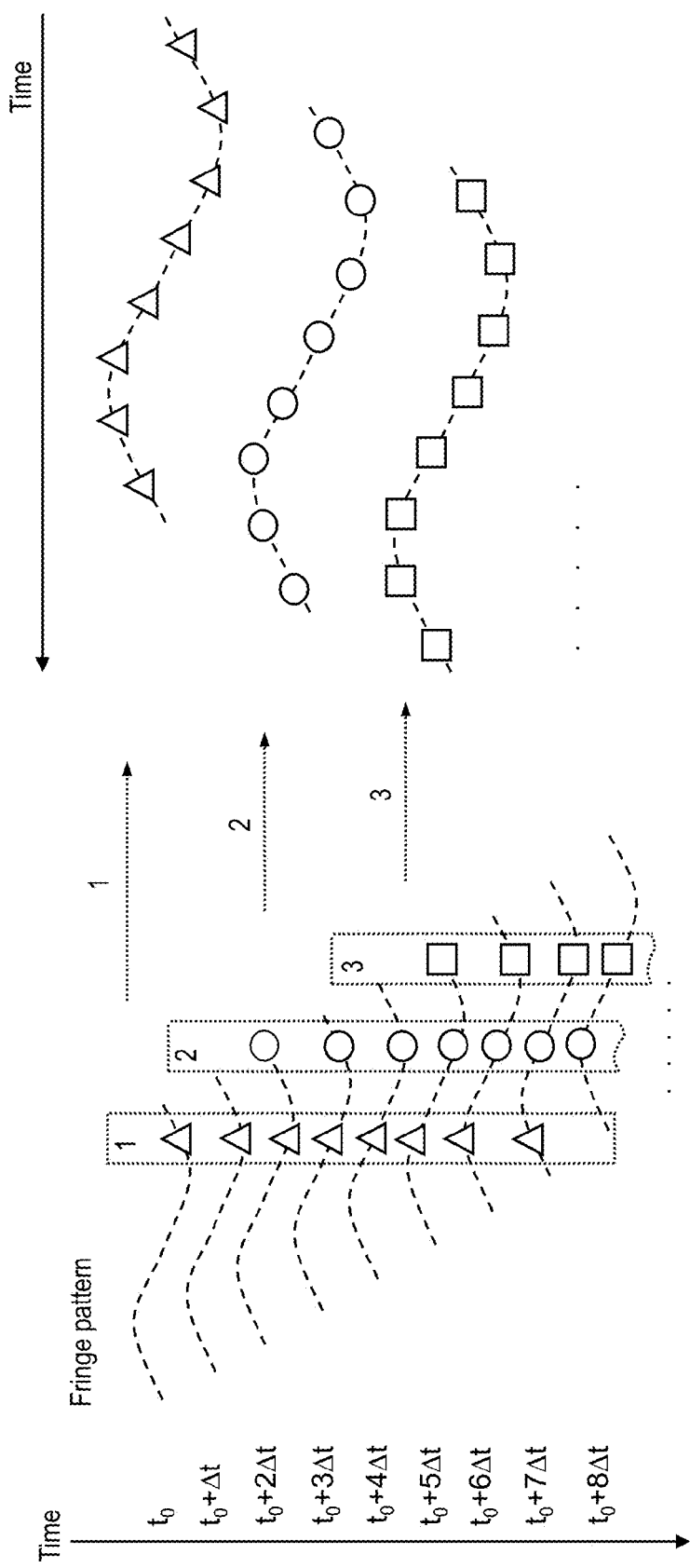
FIG. 16 is a diagram that shows schematics of image formation mechanism that retrieves the intensity curves of individual slices of the scanned object, such as triangles, circles, and squares according to embodiments of the application.

As described herein, in embodiments of tuned phase contrast imaging systems, the phase retrieval algorithm can require multiple x-ray exposures at different lateral positions of analyzer grating, which allows forming a cosine shaped intensity curve shown in FIG. 7. When the phase contrast imaging system is detuned, the detector can already measure the cosine shaped fringe pattern and the grating stepping is no longer required. Instead, in some exemplary embodiments, the grating G1, the grating G2 and the detector D can be fixed at one relative position and moved to image the object, for example attached to a swing arm, and the swing arm can be continuously moved across the stationary object. Alternatively, in one embodiment, the swing arm can be at rest and the object can be laterally moved across in the plane perpendicular to incident x-rays. FIG. 14 is a diagram that illustrates exemplary motion of interferometer with respect to objects or vise versa for a phase contrast imaging system embodiment. FIG. 15 is a diagram that illustrates exemplary of object scan schematics that project individual slices of the object onto one-period fringe pattern measured in the detector plane. Triangle, circle, and square shapes shown in FIGS. 14-15 refer to different parts of the exemplary object. When the object and the swing arm with fixed G1, G2, and D are moved relative to each other, those object parts are individually projected on different lateral positions of the fringe pattern at subsequent instances of time. After, the scan of the whole object is completed, each individual part of the object, such as triangle, circle and square, is measured several times (e.g., N=8) at different intensity. In other words, each of the exemplary shapes (e.g., triangle, circle, and square) will have their individual intensity curve similar to the one shown in FIG. 7. FIG. 16 shows the schematics of intensity curve formation for an individual slice of the object (e.g., triangles, circles, and squares). Again, the Fourier based reconstruction technique, described herein, can be applied to each of the intensity curves to form the transmission, differential phase, and darkfield images for each of the slices. Then the slice images can be combined or stitched together to form image(s) of the full object.

The functional diagram in FIG. 2 drawn for a case of a tuned PCI system can also be applied to detuned PCI system. However, for a detuned PCI system embodiment, the piezo translational stage is not required, since the grating is no longer stepped in the detuned PCI configuration.

As described herein, embodiments of phase-contrast digital imaging systems and/or methods of using the same can provide various advantages according to the application. Embodiments of a grating-based differential phase contrast digital imaging systems (e.g., mammography systems) are related to a slot scanning grating based PCI system that is detuned to use a continuous motion of the swing arm with the interferometer setup (e.g., phase grating G1, analyzer grating G2, and detector D) fixed to an arm for a moment of the swing motion. Embodiments of DR PCI imaging systems and/or methods can adjust the energy of the incident photon beam (e.g., different kVp values, exposure levels, and/or filters) based on the thickness of the object or breast. In one embodiment, a DR PCI system can have multiple G1 gratings with the same pitch, but different heights of Si structure that are selected for the corresponding mean photon energy preferably such that the phase shift created by the respective G1 grating provides desired or maximum contrast (e.g., π phase shift).

For example, embodiments of DR PCI systems and/or methods can use continuous motion of the swing arm to scan an object with FOV larger then the size of detector. Further, geometrical parameters of the gratings are set such that the interference system (i.e. G1+G2+D) is detuned (e.g., produces a fringe pattern in the plane of detector) for embodiments of DR PCI systems and/or methods. Beneficially, phase stepping (e.g., relative to grating G1, G2, or G0 motions during the scan) are not invoked.

Embodiments of DR PCI systems and/or methods can use different energy of the photon beam and/or different exposure levels (e.g., depending on the breast thickness). For example, multiple different exposure levels or three kVp settings can be used (e.g., 25, 30, and 40 kVp) where each of kVp settings can require its own phase grating (e.g., three different phase gratings can be replaceably mounted on a low absorbing holder disposed in the phase grating G1 plane). In one embodiment, each of phase gratings (e.g., G1) can have same pitch but different height of phase shifting Si structure because the phase shift is energy dependent. In one embodiment, when an x-ray tube's anode material is changed (e.g., from W to Mo), then the G1 grating holder can correspondingly be exchanged to another grating holder to match the mean energies of the new spectra (e.g., Si structure heights).

Again, the refractive index can be expressed as a complex number, where n=1−δ+iβ. The imaginary part β contributes to the attenuation of the amplitude and the real part δ (refraction index decrement) is responsible for the phase shift. When the x-ray is passing through the tissue or object, the attenuation and phase shift can be calculated as:

$$\begin{cases} \mu(x, y) = \frac{4\pi}{\lambda} \int \beta(x, y, z) dz \\ \varphi(x, y) = \frac{2\pi}{\lambda} \int \delta(x, y, z) dz \end{cases} \quad (18)$$

Figure 17B:
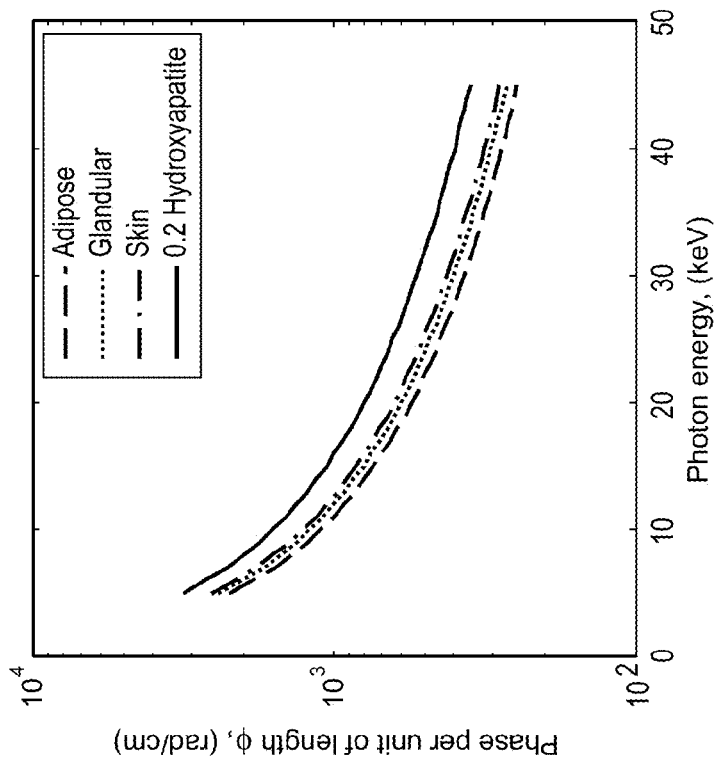
FIGS. 17(a)-17(b) are diagrams that show linear attenuation and phase shift per unit of length for various exemplary materials, respectively.
Figure 17A:
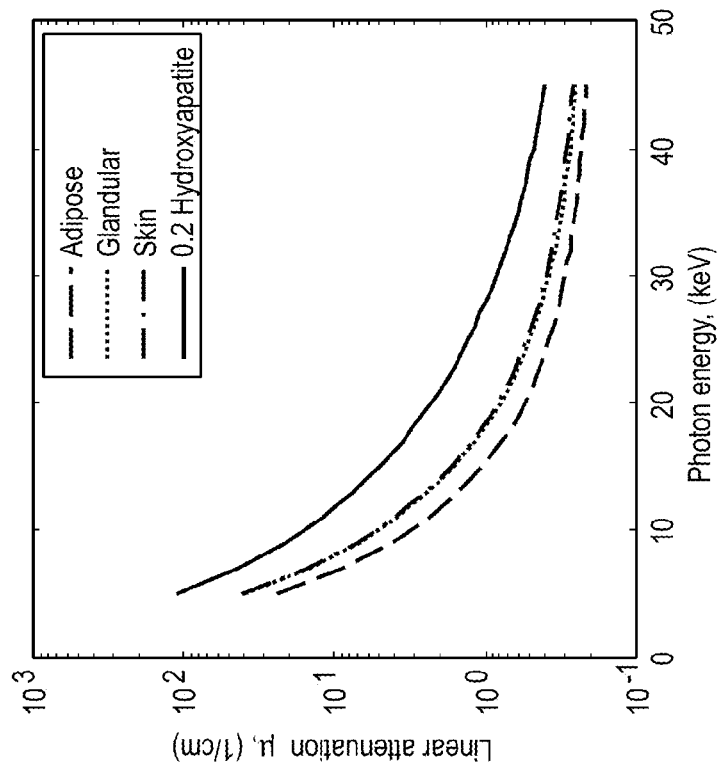
Figure 18:
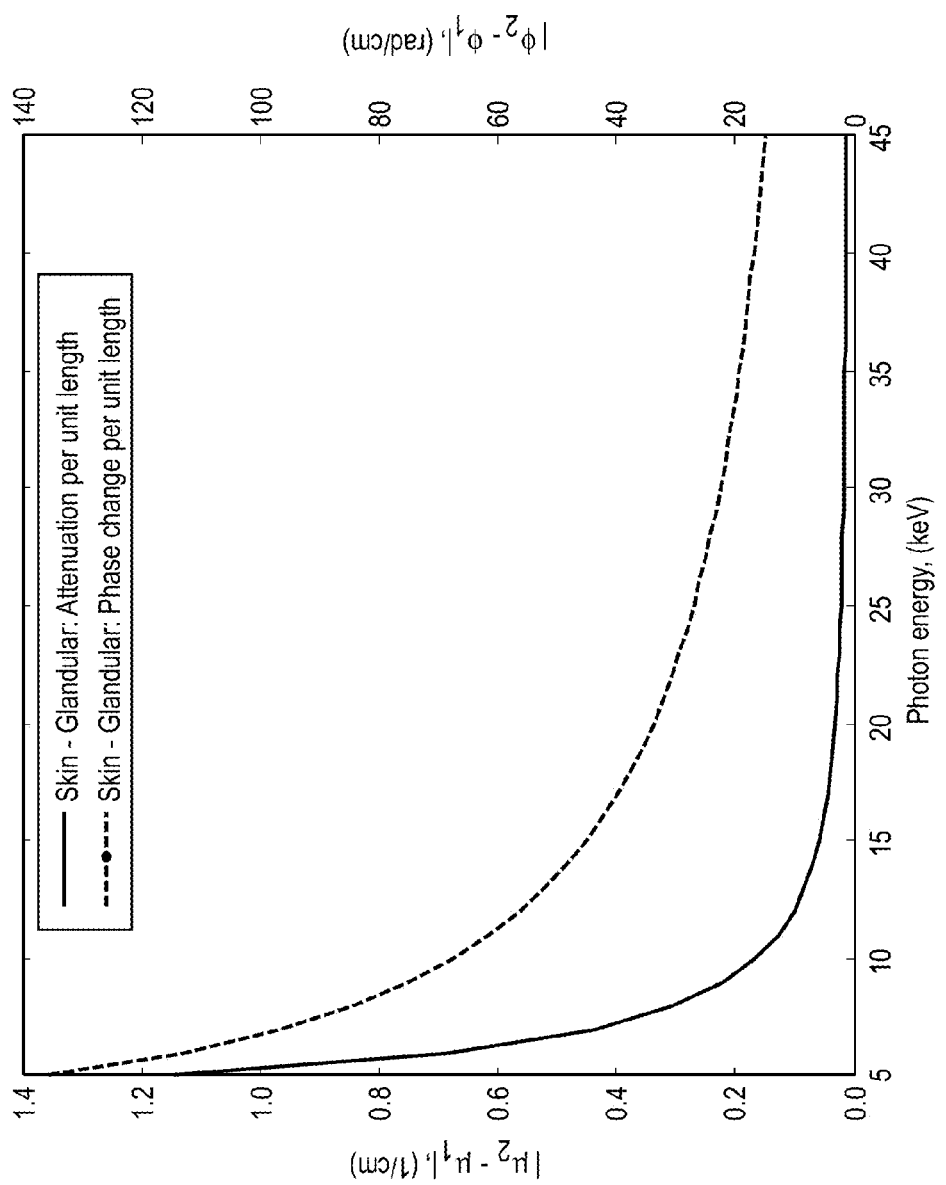
FIG. 18 is a diagram that shows absorption (left axis) and phase (right axis) contrasts between two exemplary materials.

For a compound of density ρ the refractive index can be expressed in terms of the atomic scattering factors $f_1$ and $f_2$:

$$n \cong 1 - \frac{r_e N_a \lambda^2 \rho}{2\pi} \left( \sum_k x_k (f_{1,k} + i f_{2,k}) \right) \Big/ \left( \sum_k x_k A_k \right), \quad (19)$$

where $r_e$, $N_a$, λ, and ρ are the electron radius, Avogadro number, photon wavelength, and effective density of compound, respectively. The summation is taken over the relative concentrations $x_k$ of each of the chemical elements of atomic mass $A_k$ comprising the compound. Using Equation (17) it can be shown that δ is about $10^3$ to $10^4$ times larger than β. For example, FIG. 17 shows the linear attenuation and phase shift per unit of length (e.g., 1 cm) for materials that are and can be common for a breast: adipose tissue, glandular tissue, skin, and 20% hydroxyapatite water-based mixture (e.g., which can represent a calcification). As shown in FIG. 17, the phase shift is significantly (e.g., few orders) higher then the absorption. FIG. 18 shows an example of the contrast between two materials, glandular tissue and skin, that have very similar attenuation curves and that can be virtually inseparable in standard absorption image. As shown in FIG. 18, the difference between material linear attenuations can be plotted on the left, while the difference in phase can be shown on the right. The curve for phase shift is significantly higher than the one for absorption, and therefore the image of the material phase shift should provide a better material differentiation. The absorption and phase shift curves from FIG. 17 are tabulated in Table 2 for photon energies 20, 30, and 40 keV. Additionally, the exemplary two-material absorption and phase shift differences from FIG. 18 are shown in Table 3.

Figure 19:
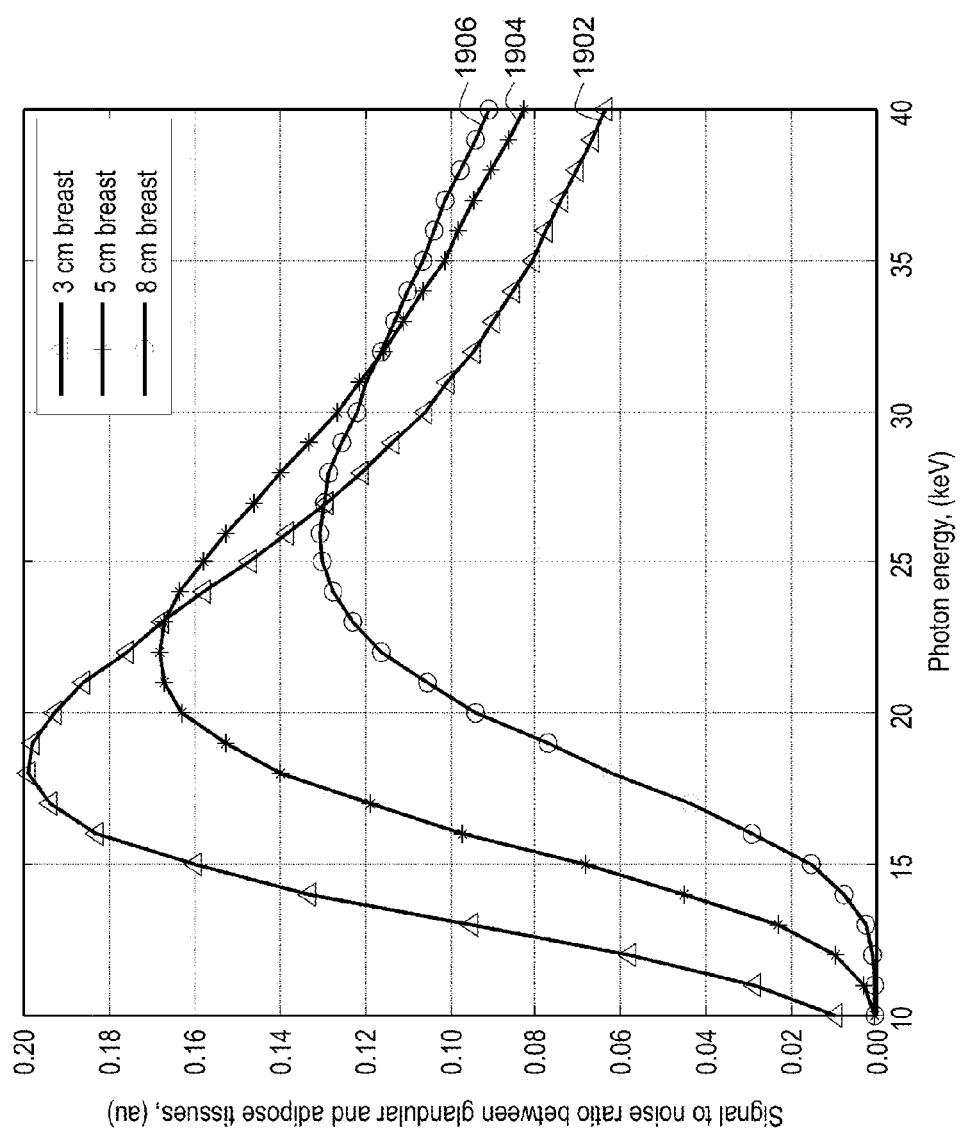
FIG. 19 is a diagram that shows signal to noise ratio between glandular and adipose tissues for different thicknesses of compressed breast.

In conventional mammography, the energy and the exposure of the x-ray typically can be altered depending on a thickness of the breast. Thinner breast can be imaged with lower kVp and lower current (e.g., for the x-ray tube), while thicker breast require higher energy x-rays for getting an image with a good contrast. FIG. 19 shows the glandular to adipose signal to noise ratio for different thicknesses of compressed breast as a function of photon energy. Curves with triangles 1902, stars 1904, and circles 1906 correspond to 3, 5, and 8 cm breast thicknesses, respectively. Also, the signal to noise ratio is estimated between two pixels, where one of the pixels contains an x-ray projection from the adipose tissue and another pixel correspond to projection from glandular tissue. The thicknesses of the tissues in the example (e.g., nearby or adjacent pixels) are equal. As shown in FIG. 19, a desired photon energy or optimal photon energy (located at the peak's maximum) can increase for thicker breast. Thus, a high or maximum SNR for 3 cm breast thickness can occur about 18 keV photon energy and a high or maximum SNR for 8 cm breast thickness can occur about 26 keV photon energy. Again, the curves 1902, 1904, 1906 were calculated with assumption that pixels contain pure glandular and pure adipose tissues. However, in a mammography scan, significant overlap between these two tissues can be present. In such a case, the desired parameters (e.g., for increased SNR) can change. For example, when a contrast between a pixel with pure glandular tissue and another pixel with a mix of adipose and glandular tissues (let say, 10% and 90%, respectively) being measured or maximized, the desired or optimal energies can change from 18.3 to 19.5 keV for 3 cm thick breast, from 21.8 to 23.4 keV for 5 cm thick breast, and from 25.8 to 27.7 keV for 8 cm thick breast. In such a case, desired or optimal energy settings drift towards higher energies for thicker breast. Accordingly, in one embodiment, 25, 30, and 40 kVp x-ray spectra, can be chosen for imaging thin, medium and thick breasts, respectively. The mean energies of the chosen x-ray spectra are 21.7, 23.3, and 28 keV, respectively, which can correspond to the deducted earlier energy

TABLE 2

Material attenuation and phase change per unit of length

| Energy, | Adipose | | Glandular | | Skin | | 0.2 Hydroxyapatite | |
|---|---|---|---|---|---|---|---|---|
| (keV) | μ, (1/cm) | φ, (rad/cm) | μ, (1/cm) | φ, (rad/cm) | μ, (1/cm) | φ, (rad/cm) | μ, (1/cm) | φ, (rad/cm) |
| 20 | 0.54 | 555.81 | 0.79 | 602.41 | 0.82 | 636.20 | 2.26 | 799.90 |
| 30 | 0.29 | 370.33 | 0.37 | 401.31 | 0.39 | 423.83 | 0.83 | 532.37 |
| 40 | 0.23 | 277.71 | 0.27 | 300.92 | 0.28 | 317.80 | 0.48 | 399.00 |

TABLE 3

Attenuation and phase differences between two materials

| | Glandular - Adipose | | Skin - Glandular | | 0.2 Hydroxyapatite - Glandular | |
|---|---|---|---|---|---|---|
| Energy, (keV) | $\|\mu_G - \mu_A\|$, (1/cm) | $\|\phi_G - \phi_A\|$, (rad/cm) | $\|\mu_S - \mu_G\|$, (1/cm) | $\|\phi_S - \phi_G\|$, (rad/cm) | $\|\mu_{HA} - \mu_G\|$, (1/cm) | $\|\phi_{HA} - \phi_G\|$, (rad/cm) |
| 20 | 0.25 | 46.60 | 0.03 | 33.79 | 1.48 | 197.49 |
| 30 | 0.08 | 30.98 | 0.02 | 22.52 | 0.46 | 131.06 |
| 40 | 0.04 | 23.21 | 0.01 | 16.89 | 0.21 | 98.08 | values. Such settings are exemplary and imaging parameters can further be adjusted to meet, for example, signal to noise performance parameters.

As described herein, geometry of the PCI system is a function of the x-ray energy. When the mean energy of the x-ray beam is changed, e.g., the spectrum is altered; embodiments herein can change distances between G0 grating and G1 (e.g., L) and between G1 and G2 (e.g., d). Additionally, phase change amount caused by the phase grating G1 should also change according to h=lambda/(2*sigma) (see equation (6). In one embodiment, a height (h) of the silicon structure in phase grating G1 can change according to h=lambda/(2*sigma). Exemplary DR PCI system parameters for different voltage settings on the x-ray tube are described in Table 4.

TABLE 4

Exemplary system parameters for different voltage settings

|  | tube voltage, V (kVp) | | |
|---|---|---|---|
|  | 25 | 30 | 40 |
| mean energy, E (keV) | 21.68 | 23.27 | 28 |
| mean wavelength, $\lambda$ (Å) | 0.572 | 0.533 | 0.443 |
| distance, L (mm) | 494 | 530 | 638 |
| distance, d (mm) | 32.9 | 35.3 | 42.5 |
| $G_0$ pitch, $p_0$ (um) | 30 | 30 | 30 |
| $G_1$ pitch, $p_1$ (um) | 3.75 | 3.75 | 3.75 |
| $G_2$ pitch, $p_2$ (um) for tuned system | 2 | 2 | 2 |
| $G_2$ pitch, $p_2$ (um) for detuned system with 0.1 cyc/mm fringe pattern frequency | 1.9996 | 1.9996 | 1.9996 |
| structure height of $G_0$ (Au), $h_0$ (um) | 42 | 42 | 42 |
| structure height of $G_1$ (Si), $h_1$ (um) | 28 | 30 | 36 |
| structure height of $G_2$ (Au), $h_2$ (um) | 26 | 26 | 26 |
| spatial coherence length, $l_c$ | 1.88 | 1.88 | 1.88 |

Figures 20A, 20B:
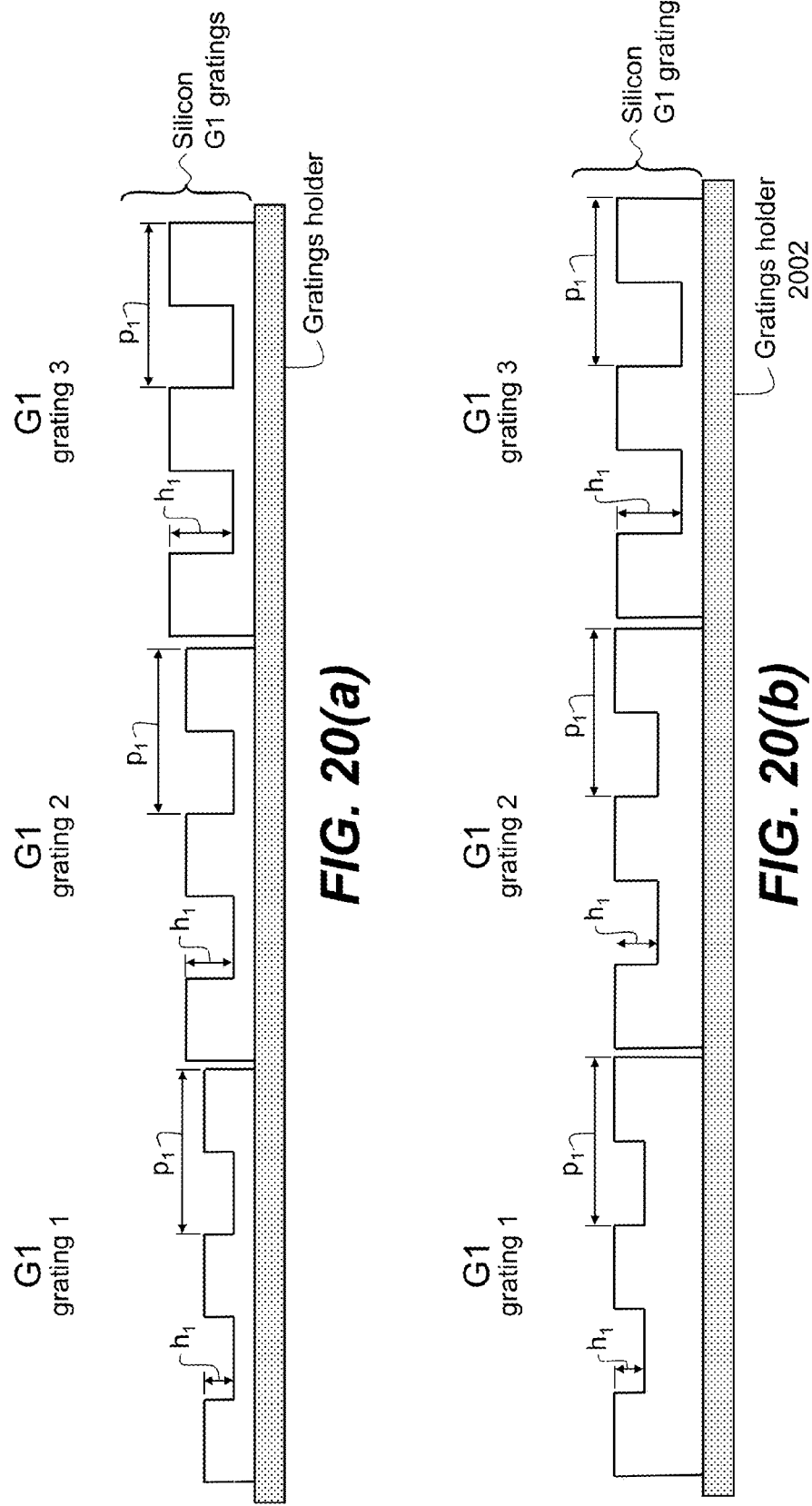
FIGS. 20(a)-20(b) are diagrams that show embodiments of three G1 gratings with same pitch p1 and different height arranged on a low absorbing holder according to the application.
Figure 21:
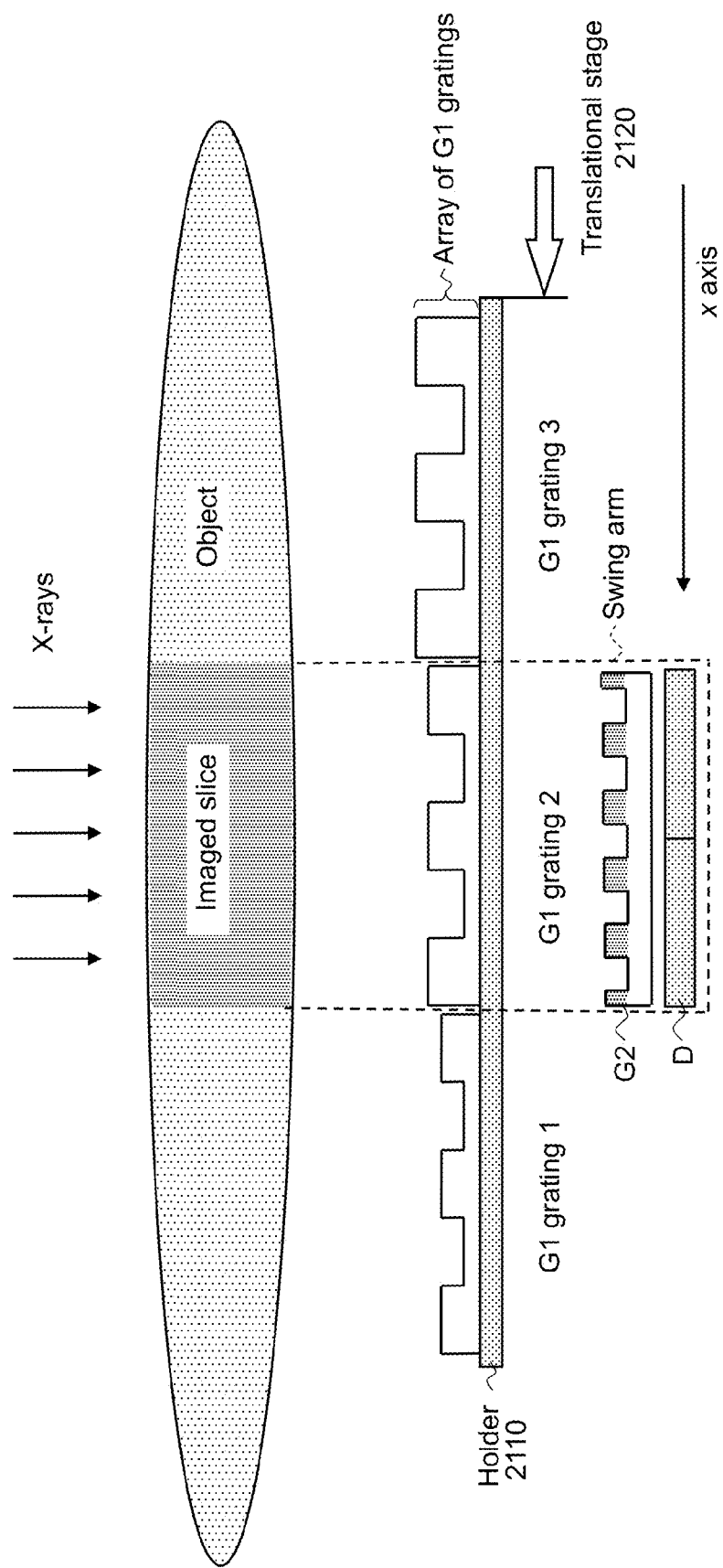
FIG. 21 is a diagram that shows schematics of the array of phase gratings G1 disposed in front of analyzer grating G2 and detector D according to the application.

In order to use different heights of phase grating structure, which can be made of Si for other materials known to one skilled in the art, the array of three phase gratings can be used. The array of gratings can have the same pitch as shown in FIGS. 20(a)-20(b). Exemplary multiple phase gratings G1 can be attached to a holder (e.g., ladder) made of low absorbing material. As shown in FIGS. 20(a)-20(b), exemplary heights for the three G1 gratings can be chosen so that the incident x-rays preferably undergo the phase shift of π. A separate, coupled or integral translation stage can be attached to a holder for moving an array of multiple phase gratings G1 (e.g., in the x direction). Depending on the breast thickness, which can be measured by the compression paddle, an appropriate tube voltage can be selected and the corresponding G1 grating can be placed in line with the interferometer setup, as shown in FIG. 21. FIG. 21 shows schematics of an array of gratings G1 phase disposed in front of a single grating G2 and a single detector D. As shown in FIG. 21, a translation stage 2120 can move the array of gratings G1 and/or an optional holder 2110 in a prescribed 3D motion such as the x direction for swapping between the multiple phase gratings G1.

The production (e.g., an etching process) of the grating shown in FIG. 20(a) may be difficult because such a configuration of gratings can require three independent etching processes. However, an initial height of the Si layer and the deepness of a recess (e.g., etch) can be controlled so that heights of the phase shifting Si structures are within the specifications and the heights of the Si layer left in the etched areas are the same among the multiple G1 gratings. Thus, an embodiment for the multiple gratings that can be concurrently etched or etched into an integral structure. A single etching mask can be used. As shown in FIG. 20(b), an alternative multiple gratings G1 embodiment can use a single Si ladder, which can be split on two or more parts, where each of the parts can be individually etched to form the trenches of substantially consistent respective deepness.

Figure 22:
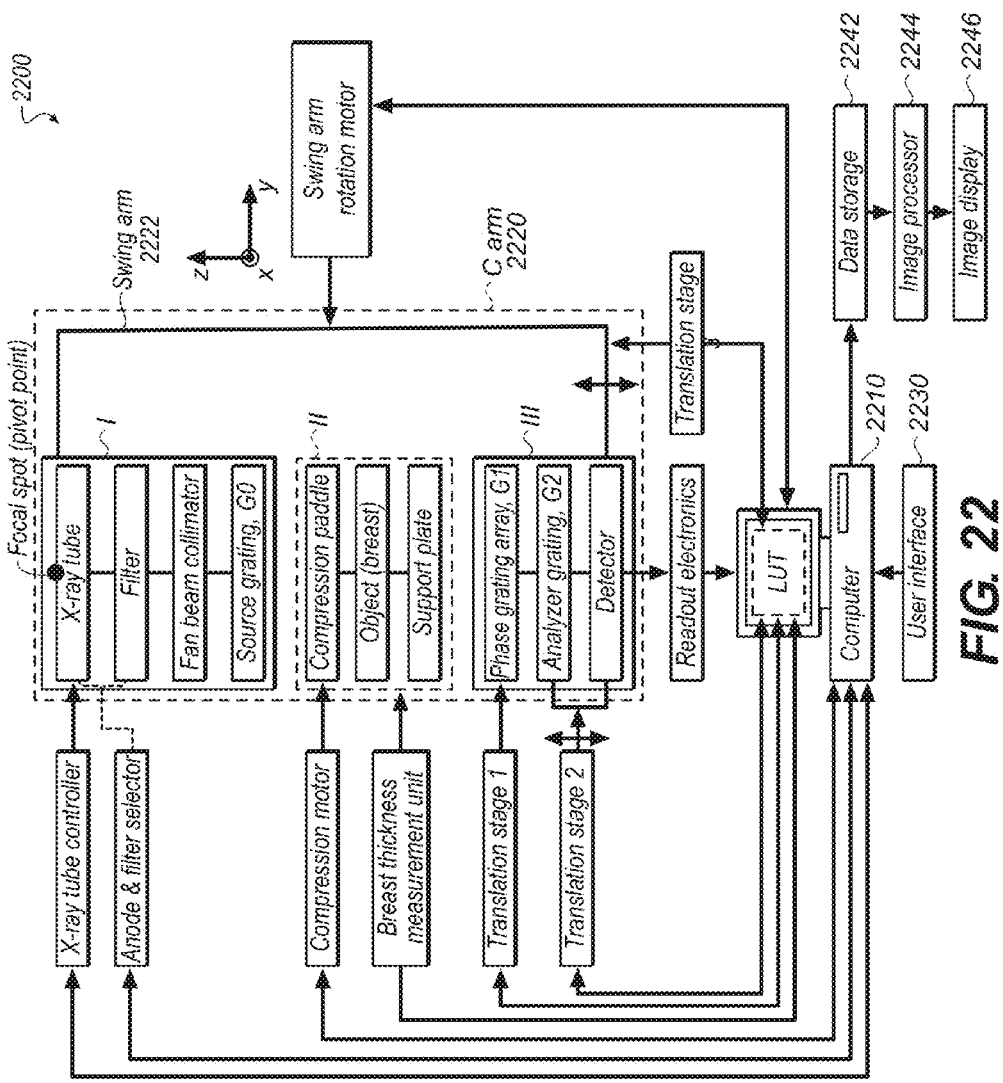
FIG. 22 is a functional block diagram that shows an embodiment of an adjustable DR PCI system that is capable of imaging different mean energies of an x-ray source.

FIG. 22 is a functional block diagram that shows an embodiment of an adjustable DR PCI system capable of imaging different mean energies of a radiation source. In typical applications, a computer or other type of dedicated logic processor for obtaining, processing, and storing image data is part of the DR PCI system, along with one or more displays for viewing image results. A computer-accessible memory is also provided, which may be a non-volatile memory storage device used for longer term storage, such as a device using magnetic, optical, or other data storage media. In addition, the computer-accessible memory can comprise an electronic memory such as a random access memory (RAM) that is used as volatile memory for shorter term data storage, such as memory used as a workspace for operating upon data or used in conjunction with a display device for temporarily storing image content as a display buffer, or memory that is employed to store a computer program having instructions for controlling one or more computers to practice method and/or system embodiments according to the application.

As shown in FIG. 22, a PCI imaging system can include or be coupled to a computer 2210. Controlled by the computer 2210, a swing arm rotation motor can be attached to a swing arm 2220 that can mount or hold x-ray unit (I) and interferometer unit (III). The x-ray unit (I) can include x-ray tube, filter, collimator, and source grating G0, while the interferometer unit (III) can include phase grating G1, analyzer grating G2, and detector D. The object can be positioned at or placed in unit (II), which can include a compression paddle and support plate for mammography or the like. All three units (I, II, and III) can be positioned by a support structure such as placed inside a C-arm 2220. For example, the unit II can have a controlled or rigid connection to the C-arm, while the swing arm 2222 can move the x-ray unit I and the interferometer III relative to the unit II. Thus, the C-arm 2220 can be rotated such that different exemplary projections of the breast (e.g., Cranio-caudal (CC) and Mediolateral Oblique (MLO)) can be taken. In one embodiment, when the compression paddle is initiated, the breast thickness can be measured by a breast thickness measurement unit. Then, a look-up table (LUT) can be used to download a corresponding PCI geometry, and translation stages 1, 2, and 3 provide necessary changes to implement the corresponding PCI geometry based on the LUT output. Translation stage 1 can swap the phase gratings G1 based on the x-ray spectrum used for imaging. Translation stage 2 can adjust relative position of the analyzer grating G2 and the detector D to the phase grating G1. The analyzer grating G2 and the detector D can be rigidly connected together or can have an additional translation stage that can adjust the distance between them. Translation stage 3 can move the interferometer unit (III) along the axis of beam propagation (e.g., z-axis). A user interface 2230 can allow the operator to control the PCI system 2200 using the computer 2210. Thus, the user interface 2230 can include the capability to set parameters for examination procedures. An x-ray tube controller, connected to a computer 2210, can control emission by the x-ray tube synchronous to the motion of the swing arm 2222. Raw data (or processed data) output by the detector D) can be stored in a data storage unit 2242, then processed by image processor 2244, and then displayed as images to operator on display 2246. In one embodiment, anode and filter selector unit 2250 can change the anode material and filter, for example from tungsten (W) to molybdenum (Mo) anode and from Aluminum (Al) filter to Mo or Rubidium (Rd). Thus, the anode material and/or the filter material can be included in the LUT.

In one embodiment, the DR PCI system can be automatically adjusted for different mean energies of an x-ray source responsive to a determination of a thickness and/or examination procedure for a series of one or more diagnostic exposures. Accordingly, once the object thickness is input for the DR PCI system, a configuration including at least phase grating selection, a first distance between the phase grating and the detector and a second distance between the phase grating and the source grating can be automatically adjusted. Then, an exposure can be initiated by the operator or automatically once the DR PCI system geometry and/or configuration corresponds to the object thickness.

Figure 10B:
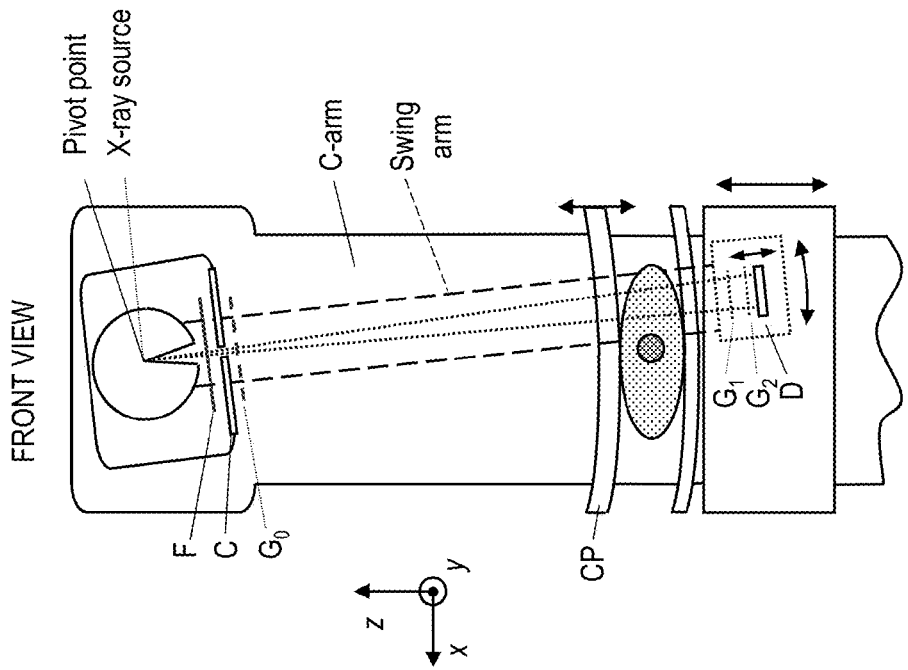
FIGS. 10A-10C are diagrams that show schematic side, front and perspective views of another slot scanning grating based phase PCI system embodiment according to the application.
Figure 10A:
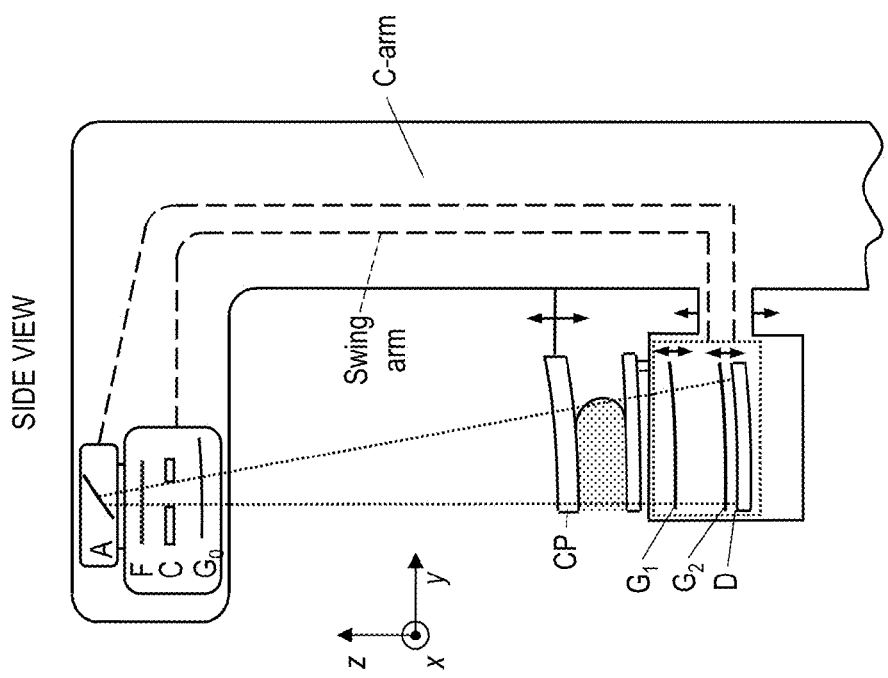
Figure 10C:
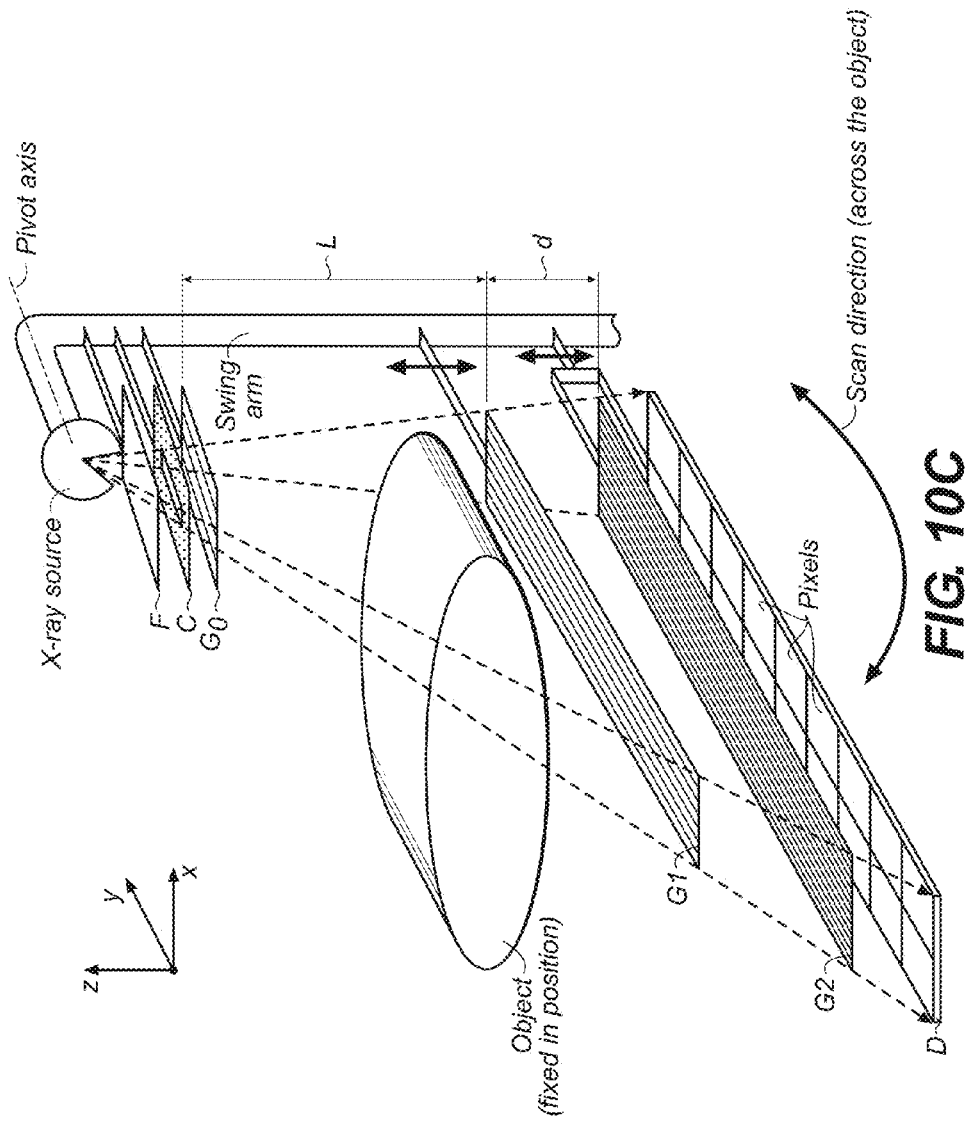
Figure 23:
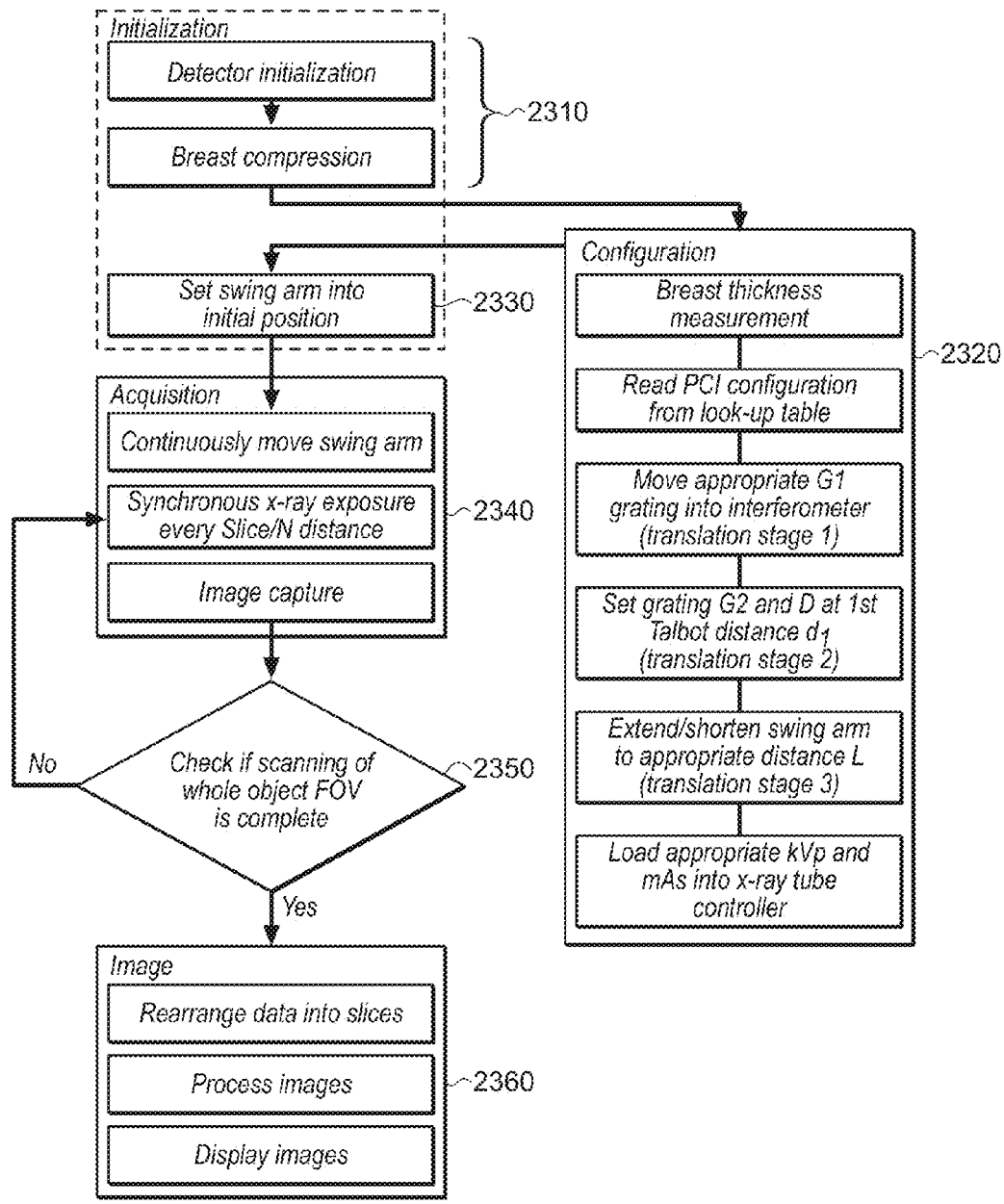
FIG. 23 is a flow chart that shows a method embodiment for operating a slot-scanning grating-based phase contrast digital mammography imaging system according to the application.

FIG. 23 is a flow chart that shows an embodiment of a method for operating a slot-scanning phase-contrast digital imaging system. The exemplary method embodiment of FIG. 23 will be described with reference to and can be implemented by the system embodiment shown in FIGS. 10A-10C, however the method is not intended to be so limited.

As shown in FIG. 23, after a process starts, an initialization can be performed (operation block 2310). An exemplary initialization can include initializing the detector in preparation for exposure. Then, the C-arm is moved into a position of a desired projection (e.g., CC or MLO). Further, the breast is compressed, which is necessary for mammographic medical imaging, and the breast thickness is measured. Depending on the breast thickness an appropriate PCI configuration can be determined (operation block 2320). In one embodiment, the PCI configuration can be read-out from look-up table (LUT). Responsive to the PCI configuration, the translation stage 1 can move the appropriate phase grating G1 into position, e.g., centered on the x-ray trajectory that connects G0, G1, and D. Then, the translation stage 2 can set the distance d between G2 and D equal to the first Talbot distance, and the distance L between G0 and G1 can be adjusted by translation stage 3. After the PCI geometry is setup, the appropriate kVp and mAs values are loaded into x-ray tube controller. Then, the swing arm is set into "neutral" position, for example, the swing arm can be vertically aligned within the C-arm (operation block 2330).

In the next step, an image acquisition can be performed (operation block 2340). Operation block 2340 can include setting the swing arm to an initial (home) position. In such a position, at least a portion to the majority part of the object is outside of C-arm's field of view (FOV). In one embodiment, no overlap, or a slight overlap with the object can be set in the C-arm's initial FOV. Then, the arm continuously moves across the object with the x-ray tube firing synchronically with the motion of the arm, and the detector can integrate, export and/or store the corresponding image data. The number of synchronous x-ray exposures can depend on the lateral size of the object and the number of data points N in one object slice, desired or needed for image reconstruction (operation block 2350, no). For example, a size of one object slice can be equal to the width of fringe pattern or detector.

The acquisition can continue until the swing arm completely clears up the object FOV (operation block 2350, yes). Then, image processing and/or display can be performed (operation block 2360). Image processing can include accessing data recorded by the detector (e.g., stored in a memory unit of a computer). Further, the data can be rearranged to form the intensity curves for each of the object slices. Then, the Fourier based reconstruction procedure can be applied. As a result, absorption, differential phase, and dark field images can be determined and/or displayed. Also, the differential phase image can be integrated and the phase shift image can be additionally presented to an operator.

In one embodiment, digital radiographic (DR) phase-contrast imaging (PCI) systems can include multiple phase gratings G1 that can be made from different or multiple materials. For example, the multiple phase gratings G1 can be different materials, which each correspond to a different anode material for a switchable x-ray source (e.g., W or Mo). Alternatively, the multiple phase gratings G1 can be different materials based on additional characteristics such as etchability or cost. In one embodiment, multiple pairs of gratings G1 and G2, or sets of gratings G0, G1, G2 can be switched for different x-ray imaging parameters such as but not limited to kVp setting, mean beam energy, object size, examination type or combinations thereof. Thus, a first pair of gratings G1a, G2a could be switched to a second pair of gratings G1b, G2b. Alternatively, a first set of gratings G0c, G1c, G2c can be switched to a second set of gratings G0d, G1d, G2d based on an object thickness or other imaging parameter.

In one embodiment, digital radiographic (DR) phase-contrast imaging (PCI) systems can include multiple phase gratings G1 that can be modify a frequency of the period of the interference pattern generated thereby (e.g., at a position of the analyzer grating G2). Thus, multiple gratings G1 can each have a different respective pitch. For example, a set of multiple phase gratings G1 could generate respective interference patterns at relative periods of 1x, 2x and 2.5x to interact with one or more analyzer gratings G2.

Conventional single-image absorption based imaging can provide relatively good contrast between bone-like and soft tissue materials. However, when the imaged object contains materials with similar absorption properties, the reliable material differentiation can become difficult or impossible because of a low relative contrast between such materials. Material differentiation limitations can be addressed by imaging the object several times using a different mean energy of x-ray beam at each exposure. This imaging approach is called spectral imaging. Spectral imaging can use the energy dependence of respective absorption coefficient to more easily perform material decomposition.

Embodiments of phase contrast imaging systems and/or methods can address or simplify the problem of material decomposition by adding the phase shift image, where contrast between materials is much greater than a contrast available in the absorption image. Although, having the phase and absorption information can significantly help in material differentiation, the discrimination between multiple materials (e.g., especially more than two) can still be difficult. Embodiments of phase contrast imaging systems and/or methods can combine spectral imaging with phase contrast imaging to allow increased material identification.

Certain exemplary embodiments can use photon-counting energy-resolving detector (e.g., CZT detector) for spectral phase contrast imaging. For example, when a 2-bin energy-resolving detector is used, embodiments described herein can get spectral information including but not limited to 1) three images (e.g., absorption, differential phase contrast, darkfield) for first energy bin and 2) another three images for second energy bin.

As described herein, to obtain desired or optimized contrast, the analyzer G2 grating has to be placed at a Talbot distance (e.g., the first Talbot distance). Talbot distances are energy dependent. Thus, different mean energy in each of multiple x-ray beams will create or use different Talbot distances. Accordingly, in the related art, to acquire images at two different mean energies, the detector or the analyzer G2 grating-detector combination should be placed at two different positions.

Embodiments of digital radiographic phase contrast imaging systems and/or methods can provide separate data/images for at least two energies using an energy resolving detector and analyzer grating at a single position during using a single scan (e.g., series of exposure(s)) of an object. Further, embodiments of digital radiographic phase contrast imaging systems and/or methods can provide two different energy exposures of an object to obtain diagnostically acceptable SNR data/images for each of the two different energy exposures without modifying a DR PCI configuration. Certain exemplary embodiments of digital radiographic phase contrast imaging systems and/or methods can implement a tuned or de-tuned arrangement of an x-ray interferometer.

Figure 24:
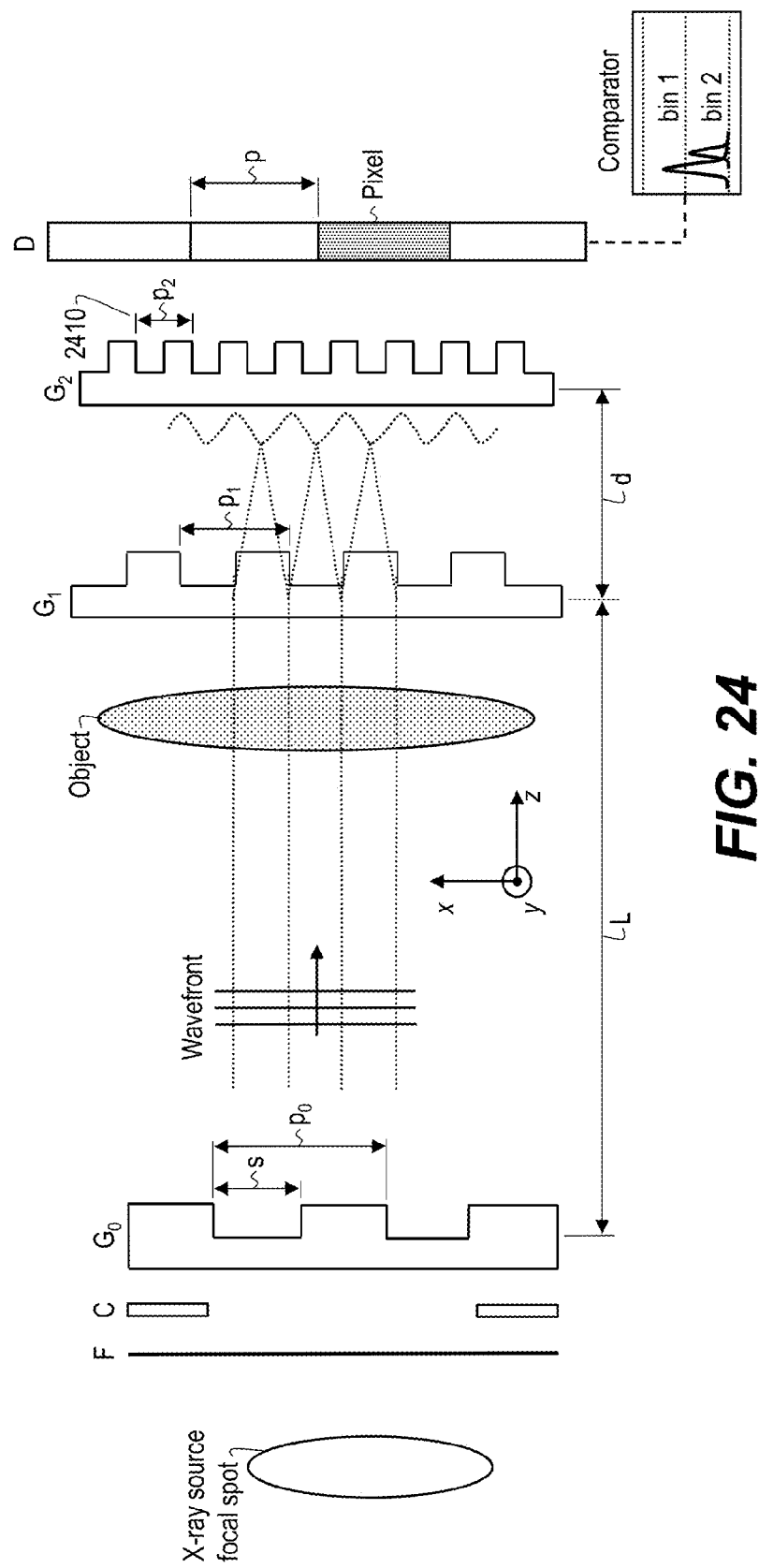
FIG. 24 is a diagram that shows yet another grating based PCI system embodiment using an energy resolving detector according to the application.

FIG. 24 is a diagram that shows an embodiment of a grating-based phase contrast imaging system using an energy-resolving detector. As shown in FIG. 24, an embodiment of a grating-based phase contrast imaging system can include a three-grating (G0, G1, G2) Talbot-Lau interferometer setup and an energy-resolving detector (e.g., photon-counting) 2410 placed behind an analyzer G2 grating. In one embodiment, an energy comparator in an imaging array or pixel of a detector (e.g., pulse height analysis) can allow energy discrimination.

Two exemplary system and/or method embodiments to implement dual energy or spectral imaging in phase contrast imaging respectively include a first embodiment using two x-ray exposures at different exposures (e.g., kVp values) and a second embodiment including only one x-ray exposure while using (at least) a two-bin energy-resolving detector. Preferably, phase contrast imaging for the second embodiment is performed using two energies from a single exposure (x-ray exposure). For such a second embodiment, the energy-resolving detector can be placed at one position only and the phase contrast imaging system can be tuned to acquire spectral images at two selected or optimized contrasts.

For the first embodiment, a conventional (e.g., indirect or direct detection) flat panel detector (e.g., area (e.g., 24×30)) can be used. Alternatively, a single energy photon-counting detector can be used. Exemplary DR PCI systems can include multiple translation stages that can, individually or in combination, change: a) distance L between multi-slit grating (source grating G0) and phase grating G1; b) distance d between gratings G1 and G2 (e.g., typically set at 1-st Talbot distance); and/or c) selection among multiple G1 gratings for positioning (e.g., in front of grating G2). The x-ray tube can be fired once for each examination. At each exposure, the kVp value can be changed and the PCI system geometry (e.g., L and d) can be adjusted such that the measured image has an increased contrast or highest contrast. Additionally, the phase shift or the height of silicon (Si) in the phase grating G1 can be such designed so that the passing x-ray experiences a phase shift of $\pi$. Again, the height of the phase grating G1 is energy dependent: $h(\lambda)=\lambda/2\delta_{Si}$, where $\delta_{Si}$ is the refractive index decrement of silicon. Exposures at different kVp values (e.g., dual values) can require an array of two G1 gratings that have the same pitch, but different height of Si structure. Both G1 gratings can be attached to a low absorbing holder (or ladder), which can be moved by translation stage to quickly place respective different G1 gratings into position for an appropriate x-ray spectrum. Table 5 shows example PCI system parameters that can be used for dual energy imaging at 30 kVp and 40 kVp x-ray spectra, respectively.

TABLE 5

Exemplary dual energy PCI system parameters

| | tube voltage, V (kVp) | |
|---|---|---|
| | 30 | 40 |
| mean energy, E (keV) | 23.27 | 28 |
| mean wavelength, $\lambda$ (Å) | 0.533 | 0.443 |
| distance, L (mm) | 530 | 638 |
| distance, d (mm) | 35.3 | 42.5 |
| $G_0$ pitch, $p_0$ (um) | 30 | 30 |
| $G_1$ pitch, $p_1$ (um) | 3.75 | 3.75 |
| $G_2$ pitch, $p_2$ (um) | 2 | 2 |
| structure height of $G_0$ (Au), $h_0$ (um) | 42 | 42 |
| structure height of $G_1$ (Si), $h_1$ (um) | 30 | 36 |
| structure height of $G_2$ (Au), $h_2$ (um) | 26 | 26 |
| spatial coherence length, $l_c$ | 1.88 | 1.88 |

In exemplary dual exposure modes, object motion or misalignment in the two scans can cause various disadvantages and can complicate material decomposition (e.g., motion artifacts). Various advantages can result from using one exposure, while spectral information is still extracted.

A single exposure that can collect spectral information for phase contrast imaging is configured with an energy-resolving detector. FIG. 25A shows the intensity of interference pattern (also called a Talbot quantum carpet) in XZ plane for a plane monochromatic wave, where the mean energy of the x-ray beam is 28 keV. As shown in FIG. 25A, a vertical axis represents the lateral dimension x scaled by the pitch of G1 grating, while a horizontal axis corresponds to the direction of wave propagation, z. Vertical lines 2512, 2514, 2516 represent Talbot distances, $d_1$, $d_2$, and $d_3$. Phase grating G1 is offset in –z direction for visual representation, however, the phase grating G1 actual position is at z=0. In FIG. 25A, the Talbot quantum carpet is plotted up to a third Talbot distance, and the interference pattern of $p_1/2$ period is repetitive for every order of Talbot distance. When a polyenergetic x-ray beam is used, the maxima of the repetitive pattern can be stretched in the z direction and the maxima intensity is degraded for higher orders of Talbot distances. FIG. 25B shows the intensity of interference pattern (also called a Talbot quantum carpet) in XZ plane for a polyenergetic wave, where the spectrum generated is the 40 kVp spectrum. Vertical lines 2522, 2524, 2526 represent Talbot distances, $d_1$, $d_2$, and $d_3$, but are no longer optimal for higher order Talbot distances.

Figure 25:
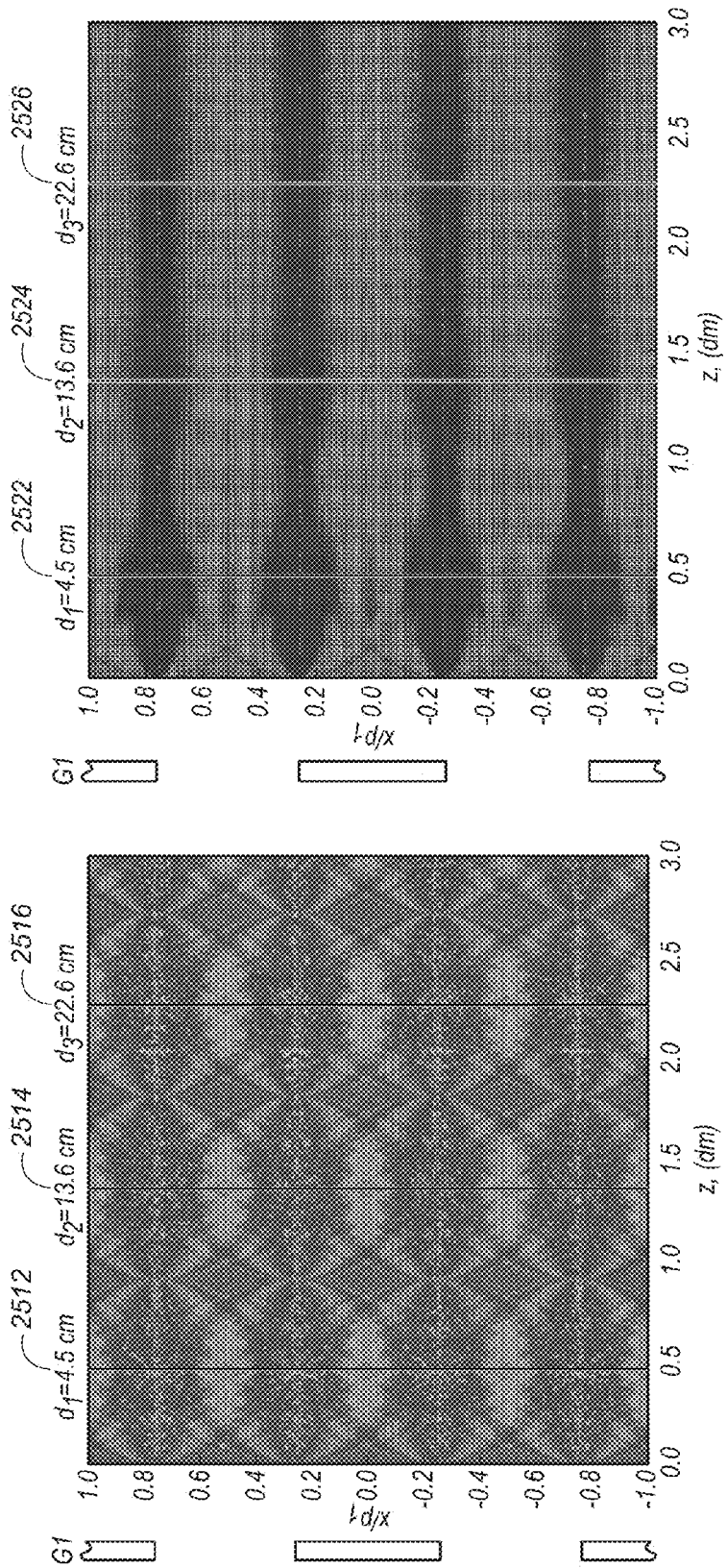
FIG. 25A-25B are diagrams that show Talbot quantum carpet for plane monoenergetic wave and plane polyenergetic wave, respectively.
Figure 26:
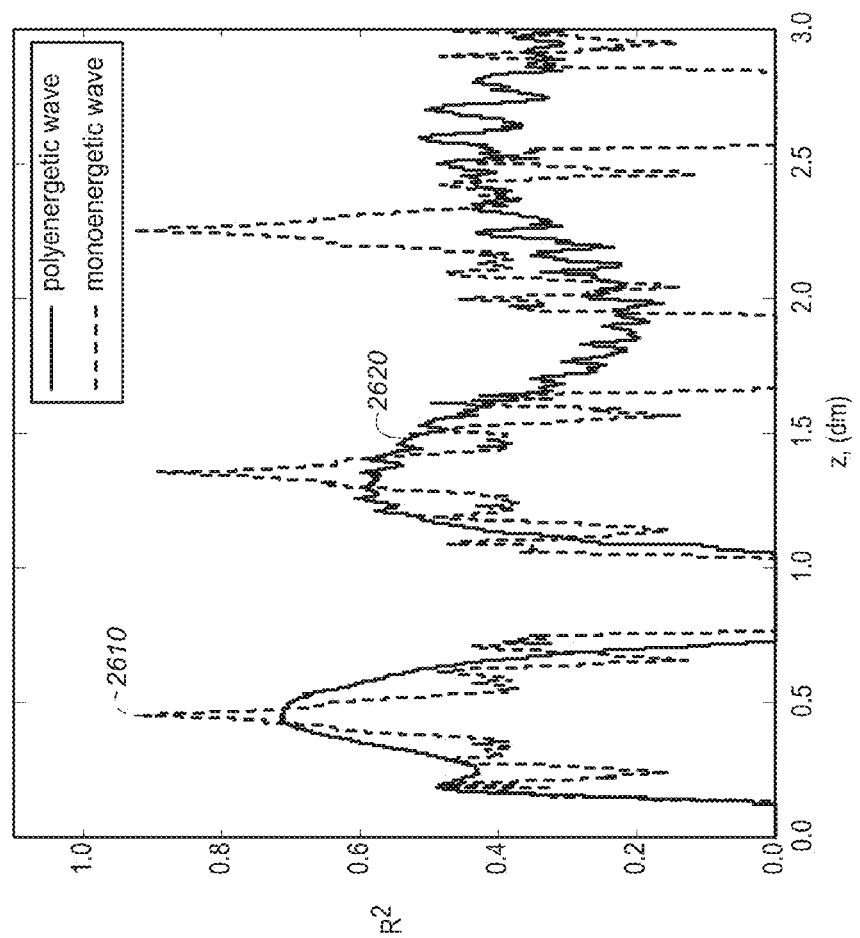
FIG. 26 is a diagram that shows correlation between expected periodic pattern and present interference pattern at each z position for mono- and polyenergetic x-ray beams, respectively.
Figure 27:
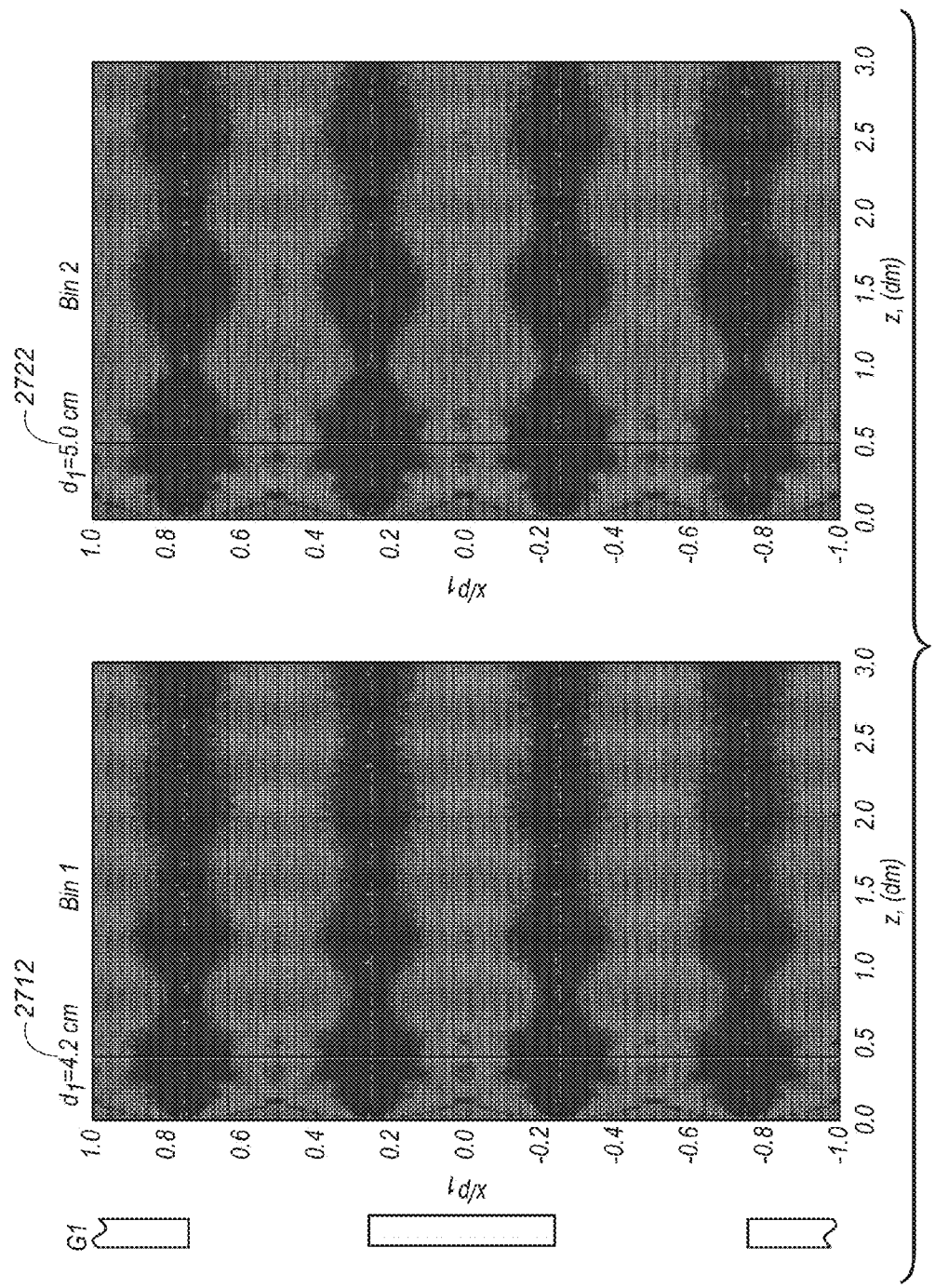
FIG. 27 is a diagram that shows Talbot quantum carpets for plane polyenergetic wave for 1st and 2nd energy bins.
Figure 28:
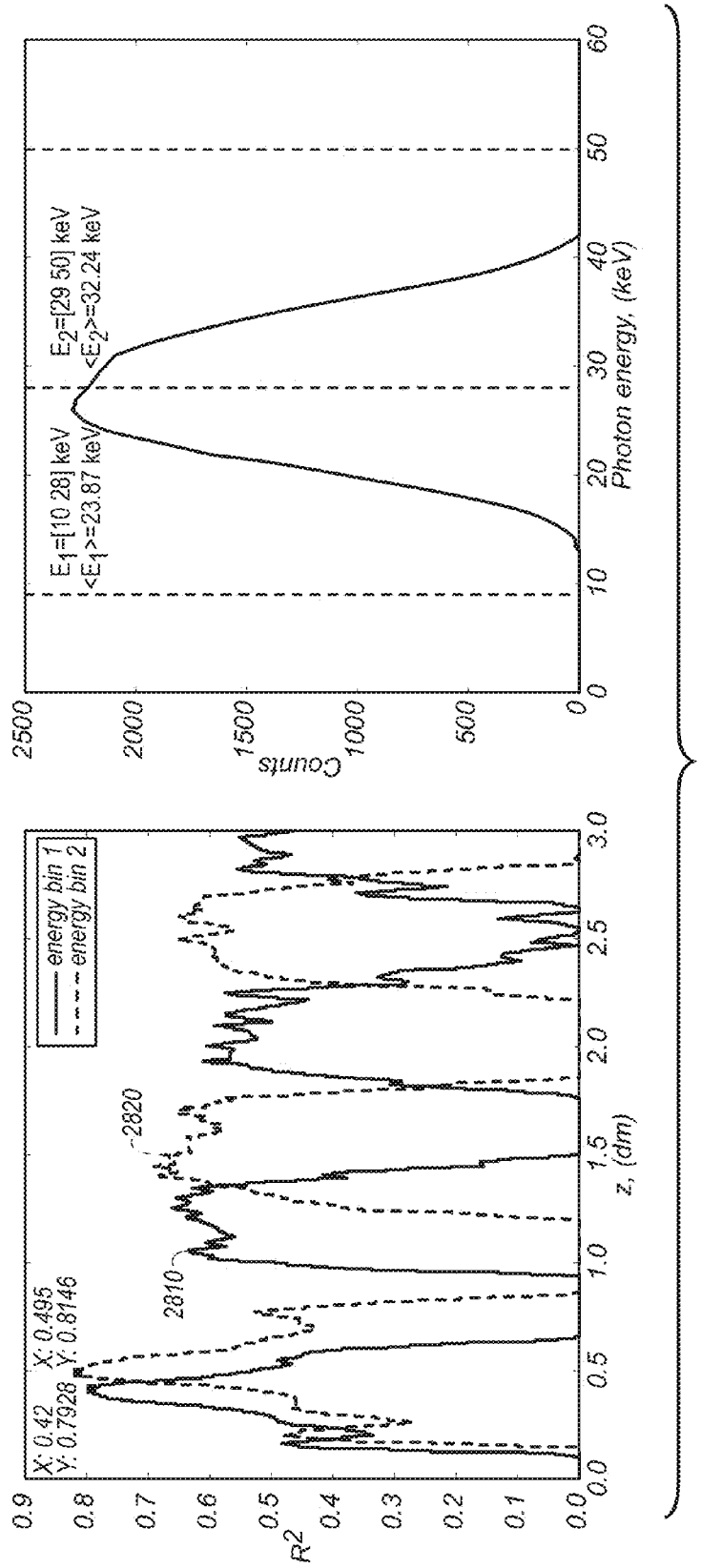
FIG. 28 is a diagram that shows (Left) correlation between expected and present interference patterns for energy bins 1 and 2; (Right) a single kVp spectrum split on two energy bins with about equal number of counts.
Figure 29:
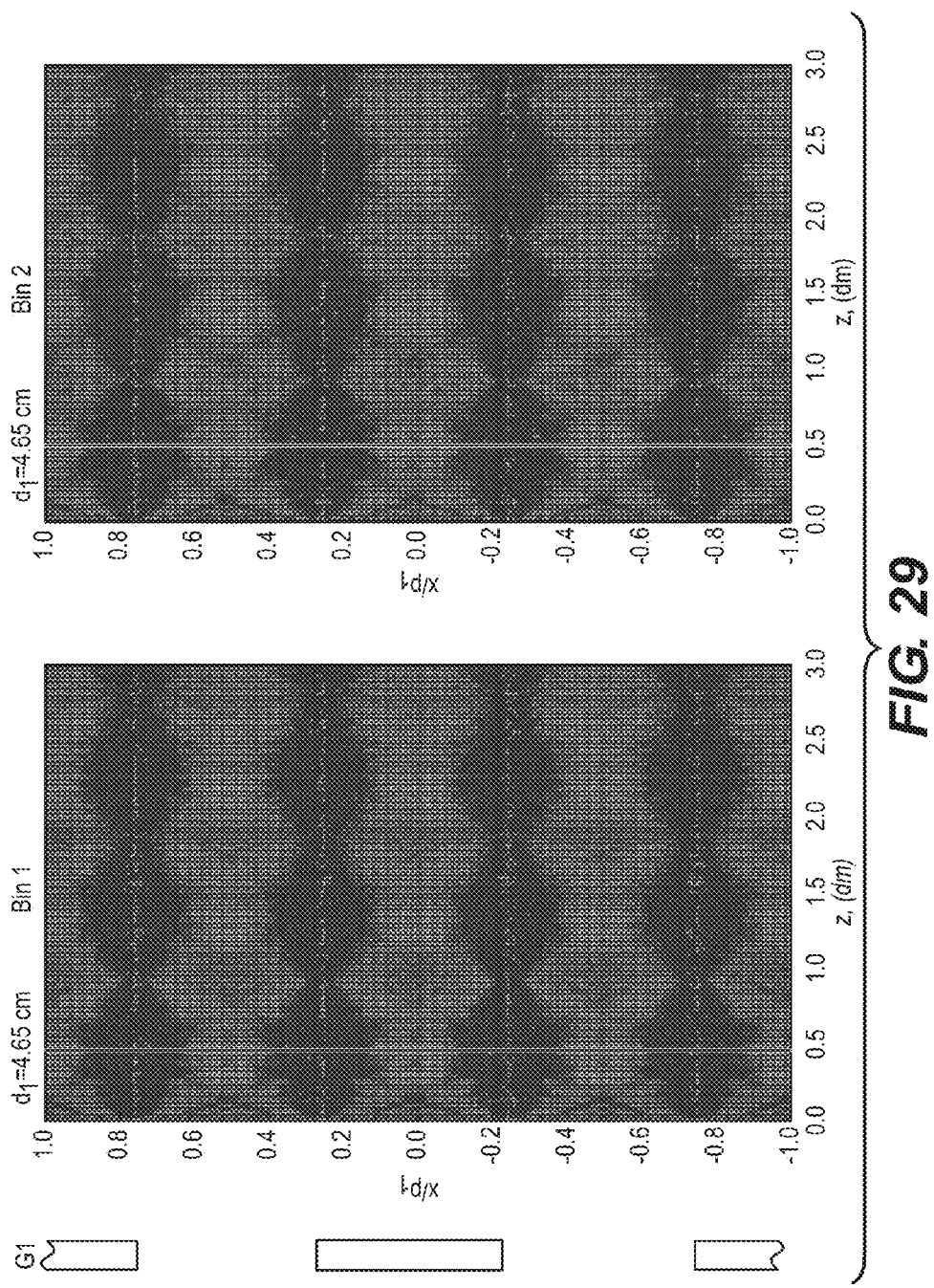
FIG. 29 is a diagram that shows Talbot quantum carpets for plane polyenergetic wave for 1st and 2nd energy bins modified to obtain equal 1st order Talbot distances according to embodiments of the application.
Figure 30:
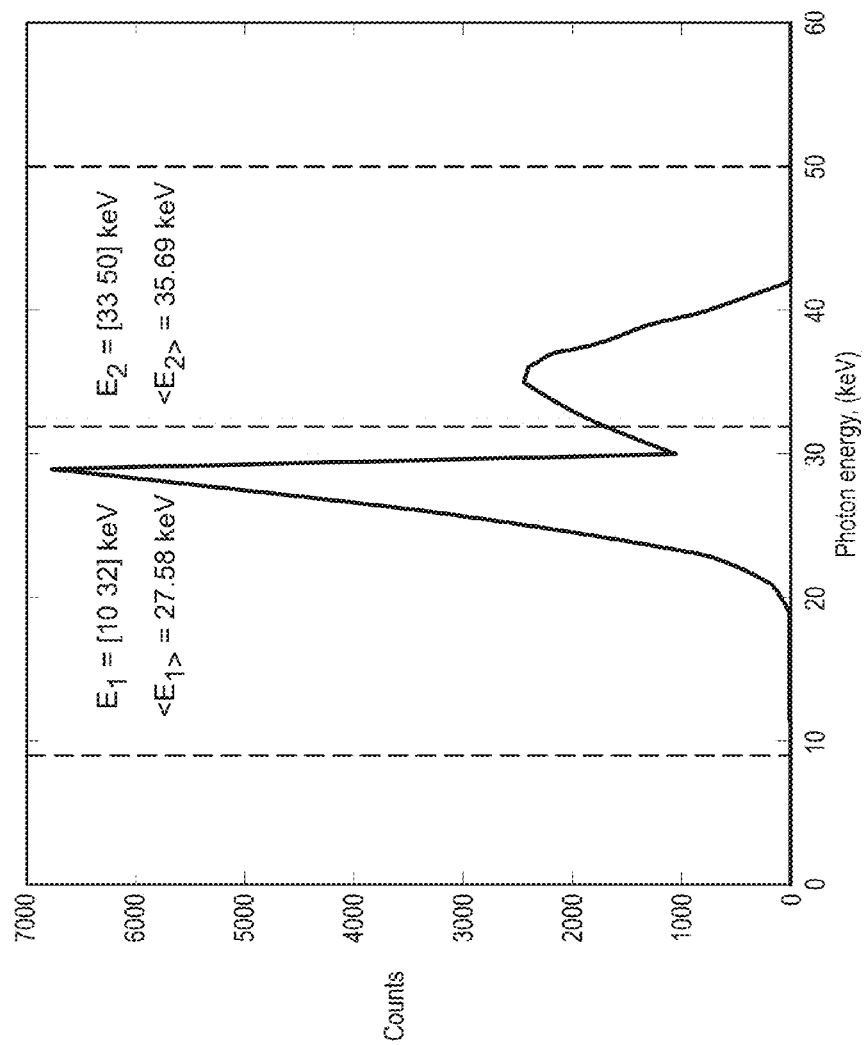
FIG. 30 is a diagram that shows a single kVp x-ray spectrum with multiple filters split on two energy bins according to embodiments of the application.
Figure 31:
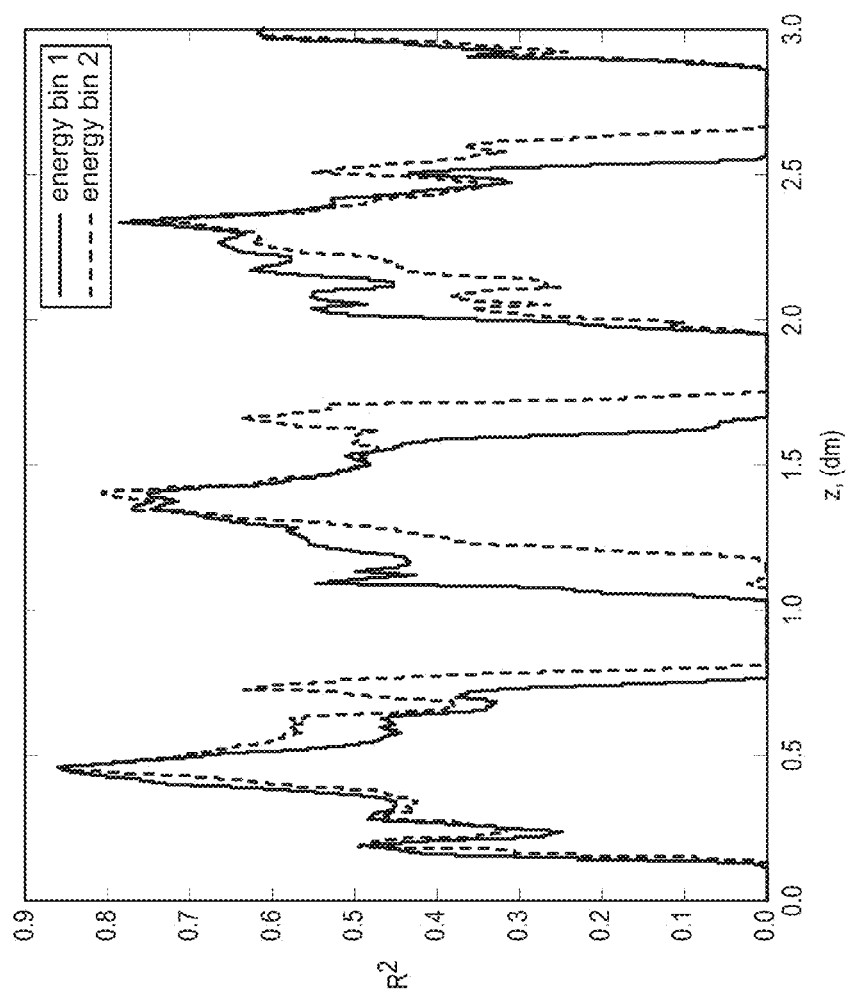
FIG. 31 is a diagram that shows correlation between expected and present interference patterns for two energy bin for a single kVp spectrum according to embodiments of the application.

To identify the positions (e.g., optimal positions), where absorption grating G2 can be placed for the polyenergetic x-ray beam, the expected periodic pattern with the pitch of $p_1/2$ was generated and compared with lateral profile at each point in z direction. Such a comparison can be done using a cross-correlation analysis. One method to determine cross-correlation can use a correlation factor $R^2$ and can use a regression analysis. FIG. 26 shows correlation factor $R^2$ as a function of wave propagation distance z. Dashed curve 2610 is the result for monoenergetic wave, and solid curve 2620 is the result for polyenergetic wave, where each curve includes three prominent peaks. As shown in FIG. 26, maxima correspond to desired positions or the optimal positions, where the absorption grating G2 can be placed. FIGS. 25A-26 correspond to a single energy acquisition, where an energy resolving capability is not present and the detector would measure data in the entire energy spectrum. When energy selectivity is invoked (e.g., energy-resolving detector is used), the quantum carpets can be estimated for each energy bin. FIG. 27 shows the quantum carpets for each of two energy bins of 40 kVp x-ray spectrum. In this case, previously wide blobs of interference pattern (see FIG. 25B) spread out leaving a well defined areas of desired or optimal positions as shown in FIG. 27. The $R^2$ correlation plots, shown in FIG. 28 (left), have two $1^{st}$ Talbot order peaks (solid 2810 and dashed 2820) more narrow in the center than the case without energy discrimination (FIG. 26). As shown in FIG. 27, selected or optimal positions of G2 are different in each of the energy bins (e.g., $d_1$=4.2 cm for bin 1 (2712) and $d_1$=5.0 for bin 2 (2722)), which is consistent with equation (7) showing Talbot distances are energy dependent. However, the selected or optimal positions on the quantum carpet significantly widen when going from monoenergetic to polyenergetic x-ray beam. Accordingly when the energy selectivity is invoked, the individual contribution from each energy bin causes redistribution of the optimal positions, as seen in FIG. 27. FIG. 29 is a diagram that shows selected energy binning and x-ray spectrum according to certain exemplary embodiments that can achieve same Talbot distance for at least two or both energy bins. Certain exemplary embodiments herein can obtain such energy binning using additional filtration. In the embodiment shown in FIG. 28 (right), optimization or selective energy binning was addressed by adding additional Tin (Sn) filtration, which can effectively transform one-peak spectrum into two-peak spectrum because of the k-edge of the tin (see also FIG. 30). The energy threshold between first and second bins was adjusted and an additional Al filtration was added such that the maxima of the first order Talbot peaks in the correlation graph are aligned as shown in FIG. 31. Also, as shown in FIG. 28 (right) control of radiation spectrum, energy threshold and/or filtration can generate a spectrum split on two energy bins with approximately equal number of counts, respectively. By modifying the Talbot distance to be the same for both energy bins can allow an energy-resolving detector to be placed at a single position or at only one plane. In the example shown in FIG. 31, the filtration was 6 mm of Al and 82 um of Sn, although embodiments are not intended to be so limited because other thicknesses and combinations of filters are contemplated and can be used as well as different multiple mean energies. Further, embodiments can modify the energy threshold between $1^{st}$ energy bin and $2^{nd}$ energy bins. Thus, certain exemplary embodiments can modify originally one-peak x-ray spectrum to divide into at least two sub-peaks that can have concurrently aligned Talbot distances for energy bins corresponding to the sub-peaks. Further analysis (e.g. cross-correlation) can be conducted for other filtrations and energy thresholds to control or optimize for contrast.

Figure 32:
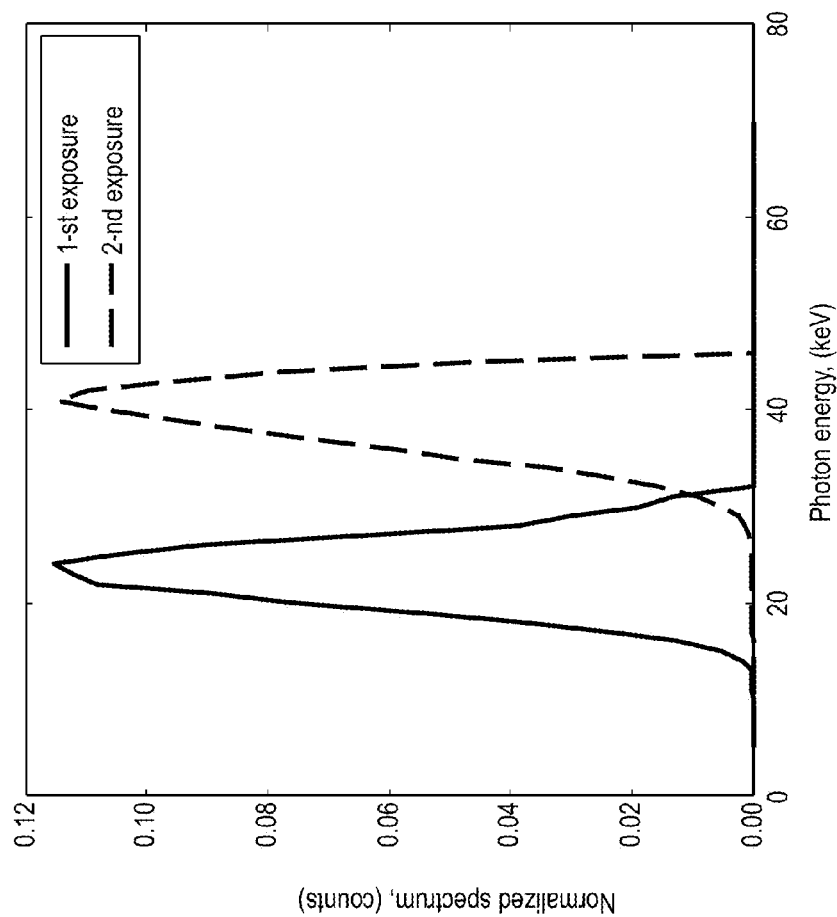
FIG. 32 is a diagram that shows exemplary spectra for two x-ray exposures according to embodiments of the application.

As described herein, when an energy resolving capability is not invoked, two x-ray exposures with different PCI geometry are required for obtaining object spectral information (e.g., See Table 5). In certain exemplary embodiments, analogous to a single exposure energy-resolving mode, two x-ray exposures, which individually produce spectra similar to the two-peaked spectrum created with a single exposure, can be determined that use a single PCI configuration or geometry. FIG. 32 is a diagram that shows a solid line spectrum 3210 that corresponds to the first exposure, and a dashed line spectrum 3220 that corresponds to the second exposure. In one embodiment, the mean energies of the spectra 3210, 3220 can match the mean energies measured at each energy bin in the case of single exposure energy-selective mode (e.g., see FIG. 30). When the spectra from two different energy level exposures are modified or optimized, the PCI geometry can be fixed (e.g., L and d). Gratings G0, G1, and G2 can be attached to a swing arm. The phase retrieval can be done either by employing phase stepping technique or by using PCI system in detuned mode, where relative positions of gratings are fixed and the continuous motion of the swing arm is employed.

Figure 33B:
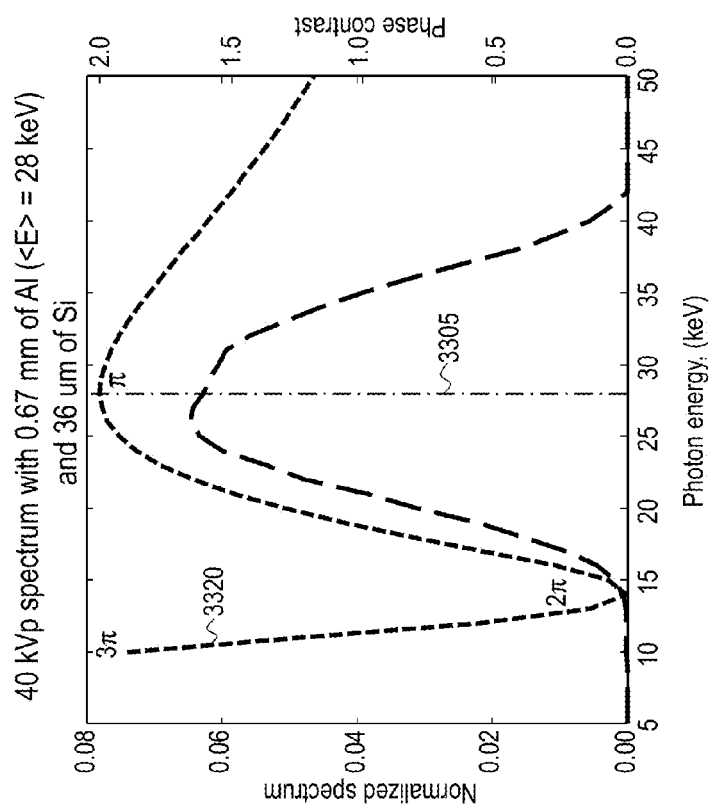
FIGS. 33A-33B are diagrams that show superimposed graphs of normalized x-ray spectrum with phase shift (right axis) caused by a G1 grating structure, and phase contrast (right axis) caused by the phase shift, respectively, according to embodiments of the application.
Figure 33A:
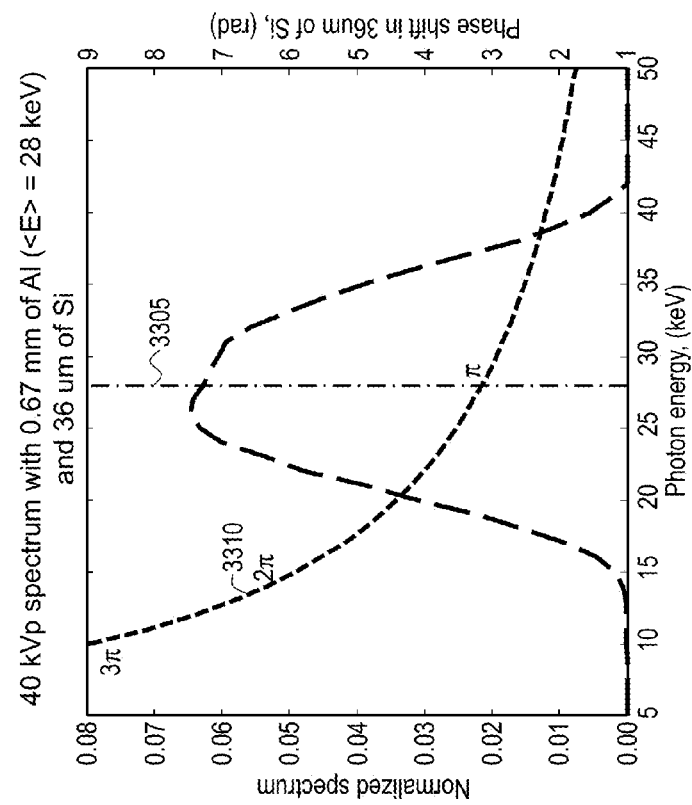
Figure 34:
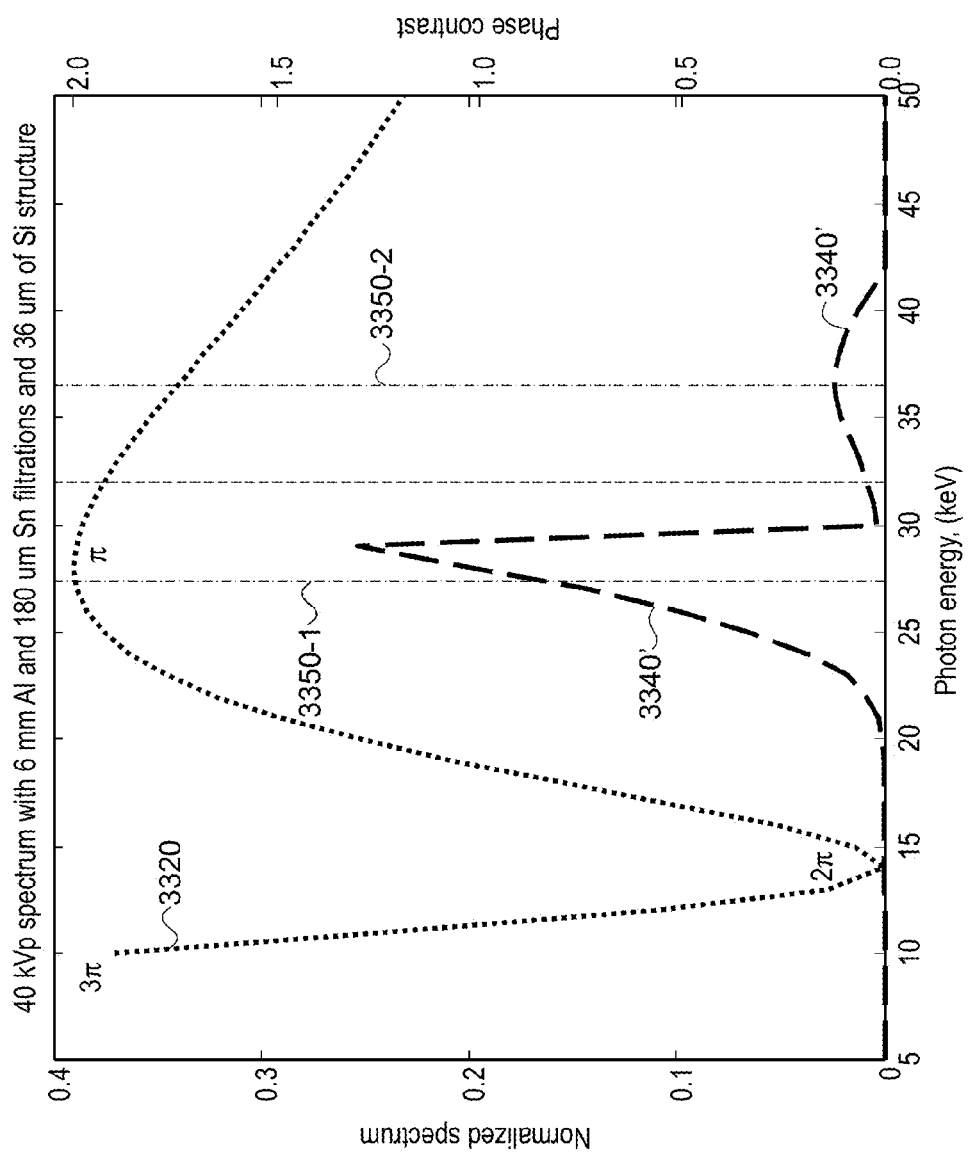
FIG. 34 is a diagram that shows superimposed graphs of a single two-peaks x-ray spectrum (left axis) and a phase contrast (right axis) for a case of energy-resolving detector. The energy threshold between first and second energy bins is denoted by dashed line, while mean energies of each bin are shown in point-dashed line.

As described herein, the phase shift caused by the phase grating G1 (e.g., Si structure) is dependent on the shape of x-ray spectrum. Accordingly, a desired height of Si structure in phase grating G1 is energy dependent. For example, to get an increased contrast or maximum contrast, the x-ray wave (e.g., mean energy) should undergo a r phase at the phase grating G1. In one embodiment, when the energy-resolving detector is used and the PCI system fires the x-ray tube only once, a single phase grating G1 can be used. Below is the analysis of how the phase shift caused by Si structure is dependent on the shape of x-ray spectrum. FIG. 33A shows superimposed graphs of 40 kVp normalized x-ray spectrum with phase shift 3310 caused by the G1 grating Si structure (right axis), and FIG. 33B shows superimposed graphs of the 40 kVp normalized x-ray spectrum with caused wave amplitude or phase contrast 3320 (right axis) caused by the phase shift. The dash-dotted line 3305 shown in FIGS. 33A-33B corresponds to the mean energy of the spectrum. To achieve increased or the maximum contrast, the x-ray wave should undergo a $\pi$ phase, which results in the splitting the beam into the ±1 diffraction orders (or wave amplitude of 2). As shown in FIG. 33A, lower energies of the x-ray experience a higher phase shift, while the phase shift is smaller for the larger energy. For a wide energy range of x-ray spectrum, there could be more than one $\pi$ phase shift. FIG. 33A shows more than $3\pi$ phase shift for the 40 kVp normalized x-ray spectrum. Every time when a $\pi$ phase shift occurs, the amplitude 3320 of phase interference can show a change between maximum and minimum, as shown in FIG. 33B. Since photons that belong to the energy range where the wave amplitude is high or maximum can create improved or the best contrast, it is desirable to have an x-ray spectrum where the contribution to the low wave amplitude regions is reduced or minimal. For example, the left edge or tale of the 40 kVp spectrum 3340 belongs to the non-optimal contrast region. According to one embodiment, the left edge of the spectrum 3340 can be shifted towards higher energies (e.g., by adding an additional filtration). FIG. 34 shows the 40 kVp normalized x-ray spectrum 3340' superimposed with the wave amplitude 3320 caused by the phase grating G1 phase shift. The case of two energy bins is shown in FIG. 34 where the dash-dotted lines 3350-1, 3350-2 correspond to the mean energies of the first and second energy bins, respectively. The parameters of filtration and the value of energy threshold between the first and second energy bins can be the same as for FIG. 30. As shown in FIG. 34, the contrast for lower energy image may be higher than higher energy bin, which can be further adjusted or equalized (e.g., spectrum optimized) by adjusting filtration (e.g., less filtration can shift the spectrum slightly left) and/or adjusting/reducing the voltage applied to an x-ray tube.

Embodiments of slot-scanning grating-based differential phase contrast systems and/or methods can provide a wide range of potential applications including medical imaging, small-animal imaging, security screening, industrial non-destructive testing, and food inspection. Embodiments according to the application can also be used for phase-contrast applications using other forms of radiation such as neutron and atom beams. Embodiments according to the application can provide a robust and low-cost phase-contrast mammography system with high efficiency and large field of view for clinical applications.

Further, when embodiments according to the application (e.g., grating-based PCI) are combined with a tomographic scan, the three-dimensional distribution of x-ray refraction index in the object as well as the distribution of absorption coefficient commonly obtained in absorption tomography can be reconstructed.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A digital radiographic (DR) phase-contrast imaging (PCI) system comprising:
   an x-ray source for radiographic imaging;
   a beam shaping assembly comprising a source grating G0; and
   an x-ray grating interferometer comprising, a phase grating G1, and
   an analyzer grating G2;
   where a single arrangement of the beam shaping assembly, the x-ray grating interferometer and a position of the detector is configured to provide at least two images obtained at different relative beam energies.

2. The system of claim 1, where the at least two images provide spectral phase contrast imaging for an object to be imaged.

3. The system of claim 1, comprising an area x-ray detector.

4. The system of claim 1, where the at least two images are obtained using an energy resolving detector and a single x-ray exposure.

5. The system of claim 1, where the at least two images are obtained using a charge integrating detector and two x-ray exposures at different energies.

6. The system of claim 5, where the DR PCI is automatically adjusted for the different mean energies of the x-ray source, where the automatic adjustment comprises modification of the mean energy of current of the x-ray source.

7. The system of claim 5, where the two x-ray exposures include reciprocal scanning motion of the x-ray source.

8. The system of claim 1, where the DR PCI system is detuned.

9. The system of claim 8, where a pitch of the analyzer G2 grating and a pitch of interference pattern produced by the phase G1 grating at the analyzer G2 grating or at the Talbot distance are not equal.

10. The system of claim 9, where a difference in the analyzer grating G2 pitch and the interference pattern pitch produced by the phase G1 grating at the analyzer G2 grating is sufficient to produce a fringe pattern is greater than 0.1 cm, or the fringe pattern is over a significant portion of the analyzer grating G2.

11. The system of claim 8, where a measurement of at least one of phase term, peak amplitude term, or dc term can be obtained from an image data set obtained in a single pass.

12. The system of claim 1, where the DR PCI system is tuned, where a pitch of the analyzer G2 grating and pitch of interference pattern produced by the phase G1 grating at the analyzer G2 grating at the Talbot distance are substantially equal.

13. The system of claim 1, where an image data set generated by a single pass of the system relative to an object is used to construct multiple images of the object including at least one of absorption contrast images, differential phase contrast images, phase shift contrast images, and dark-field images.

14. The system of claim 1, where the system can be moved to a patient height to place a compression paddle at a prescribed height, where a distance between the x-ray source and a detector holding device or detector bucky is set to a prescribed value.

15. The system of claim 1, where the phase-contrast DR imaging system is a slot-scanning phase-contrast DR imaging system.

16. The system of claim 1, where the DR PCI is configured with switchable multiple G1 gratings for the different examination types, imaging series or body parts, where the multiple G1 gratings cause different phase shift properties, where the multiple G1 gratings are implemented of the same material and have different respective heights.

17. The system of claim 1, where the DR PCI system comprises a rotational alignment mechanism to align the phase G1 grating and the analyzer G2 grating, where the rotational alignment mechanism is configured to angularly move at least one of the phase G1 grating and the analyzer G2 grating.

18. A method, comprising:
   providing an x-ray generator for radiographic imaging;
   providing a beam shaping assembly comprising a beam limiting apparatus and a source grating G0;
   providing an x-ray grating interferometer comprising a phase grating G1, and an analyzer grating G2;
   offsetting a pitch of the analyzer grating G2 relative to a pitch of an interference pattern produced by the phase grating G1 at a prescribed distance from the phase grating G1; and
   generating at least two images obtained at different relative beam energies by scanning the x-ray grating interferometer and an energy resolving detector once where an arrangement of the beam shaping assembly, the x-ray grating interferometer and a position of the detector is unchanged during the scan.

* * * * *

UNITED STATES PATENT AND TRADEMARK OFFICE
CERTIFICATE OF CORRECTION

PATENT NO.        : 9,001,967 B2
APPLICATION NO.   : 13/729443
DATED             : April 7, 2015
INVENTOR(S)       : Pavlo Baturin et al.

It is certified that error appears in the above-identified patent and that said Letters Patent is hereby corrected as shown below:

In the specification

| | |
|---|---|
| Column 9, Line 31 | Replace the word "$1_c$" with the word -- $\ell_c$ -- |
| Column 9, Line 63 | Replace the word "$1_c$" with the word -- $\ell_c$ -- |
| Column 13, Line 31 | Replace the word "20/1.8=160" with the word -- 20/1·8=160 -- |
| Column 26, Line 6 | Replace the word "r" with the word -- $\pi$ -- |

Signed and Sealed this
Fifth Day of January, 2016

Michelle K. Lee
*Director of the United States Patent and Trademark Office*